US011026850B2

(12) United States Patent
Miyama et al.

(10) Patent No.: US 11,026,850 B2
(45) Date of Patent: Jun. 8, 2021

(54) NONWOVEN FABRIC FOR OUTER SHEET OF ABSORBENT ARTICLE, AND ABSORBENT ARTICLE INCLUDING THE NONWOVEN FABRIC AS OUTER SHEET

(71) Applicant: UNICHARM CORPORATION, Ehime (JP)

(72) Inventors: Takuya Miyama, Kagawa (JP); Satoru Sakaguchi, Kagawa (JP); Masashi Uda, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 344 days.

(21) Appl. No.: 16/066,694

(22) PCT Filed: Oct. 13, 2016

(86) PCT No.: PCT/JP2016/080408
§ 371 (c)(1),
(2) Date: Jun. 28, 2018

(87) PCT Pub. No.: WO2017/115523
PCT Pub. Date: Jul. 6, 2017

(65) Prior Publication Data
US 2019/0000692 A1 Jan. 3, 2019

(30) Foreign Application Priority Data
Dec. 28, 2015 (JP) .............................. JP2015-257476

(51) Int. Cl.
*A61F 13/15* (2006.01)
*A61F 13/514* (2006.01)
(Continued)

(52) U.S. Cl.
CPC .. *A61F 13/51484* (2013.01); *A61F 13/15203* (2013.01); *A61F 13/49413* (2013.01);
(Continued)

(58) Field of Classification Search
CPC .......... A61F 13/51484; A61F 13/15203; A61F 13/514; A61F 2013/15406;
(Continued)

(56) References Cited

U.S. PATENT DOCUMENTS 5,015,245 A 5/1991 Noda
6,025,050 A * 2/2000 Srinivasan ................ B32B 5/02
428/137
(Continued)

FOREIGN PATENT DOCUMENTS

EP 1166731 A2 1/2002
JP H9-505218 A 5/1997
(Continued)

*Primary Examiner* — Jacqueline F Stephens
(74) *Attorney, Agent, or Firm* — Hauptman Ham, LLP

(57) ABSTRACT

A nonwoven fabric for an outer sheet of an absorbent article has a liquid-impermeable sheet having moisture vapor permeability, the nonwoven fabric having a thickness direction and a planar direction, and a first surface and a second surface, the nonwoven fabric including thermoplastic resin fibers, and cellulosic fibers that are cellulosic fibers of which at least a portion form a plurality of fiber masses, the nonwoven fabric comprising a plurality of gaps that are adjacent to first regions of each of the plurality of fiber masses that are facing the first surface, wherein each of the plurality of fiber masses are not joined with the thermoplastic resin fibers.

15 Claims, 10 Drawing Sheets

(51) Int. Cl.
  *B32B 5/26* (2006.01)
  *D04H 1/559* (2012.01)
  *D04H 1/541* (2012.01)
  *A61F 13/494* (2006.01)
  *A61L 15/22* (2006.01)
  *A61F 13/51* (2006.01)

(52) U.S. Cl.
  CPC .......... *A61F 13/514* (2013.01); *A61L 15/225* (2013.01); *B32B 5/26* (2013.01); *D04H 1/541* (2013.01); *D04H 1/559* (2013.01); *A61F 2013/1556* (2013.01); *A61F 2013/15406* (2013.01); *A61F 2013/4948* (2013.01); *A61F 2013/51007* (2013.01); *A61F 2013/51019* (2013.01); *A61F 2013/51026* (2013.01); *A61F 2013/51038* (2013.01)

(58) Field of Classification Search
  CPC ...... A61F 2013/1556; A61F 2013/4948; A61F 2013/51007; A61F 2013/51019; A61F 2013/51026; A61F 2013/51038; A61L 15/225; D04H 1/541; D04H 1/559; B32B 5/26
  See application file for complete search history.

(56) References Cited

U.S. PATENT DOCUMENTS

| | | | |
|---|---|---|---|
| 6,903,034 | B1* | 6/2005 | Putnam .................... D04H 3/11 428/222 |
| 2001/0053899 | A1 | 12/2001 | Mizutani et al. |
| 2002/0064624 | A1 | 5/2002 | Mizutani et al. |
| 2013/0236700 | A1 | 9/2013 | Yamanaka et al. |
| 2015/0297424 | A1 | 10/2015 | Ota et al. |
| 2015/0314560 | A1* | 11/2015 | Kauschke ......... A61F 13/15203 428/141 |
| 2018/0140479 | A1 | 5/2018 | Uda et al. |

FOREIGN PATENT DOCUMENTS

| | | |
|---|---|---|
| JP | 2002-651 A | 1/2002 |
| JP | 2002-159531 A | 6/2002 |
| JP | 2012162842 A | 8/2012 |
| JP | 2015211915 A | 11/2015 |
| JP | 5829326 B1 | 12/2015 |
| JP | 5829327 B1 | 12/2015 |
| JP | 5829349 B1 | 12/2015 |
| WO | 95/13776 A1 | 5/1995 |

\* cited by examiner

NONWOVEN FABRIC FOR OUTER SHEET OF ABSORBENT ARTICLE, AND ABSORBENT ARTICLE INCLUDING THE NONWOVEN FABRIC AS OUTER SHEET

RELATED APPLICATIONS

The present application is a National Phase of International Application No. PCT/JP2016/080408, filed on Oct. 13, 2016, and claims priority to Japanese Application No. 2015-257476, filed on Dec. 28, 2015.

FIELD

The present disclosure relates to a nonwoven fabric for an outer sheet of an absorbent article, and to an absorbent article comprising the nonwoven fabric as an outer sheet.

BACKGROUND

For absorbent articles such as disposable diapers and sanitary napkins, nonwoven fabrics have been studied that include cotton as natural fiber for the material composing the absorbent article, in order to obtain the feeling of assurance that is provided by natural materials.

As an example of such a nonwoven fabric, PTL 1 describes a surface layer that includes hydrophobic fibers and hydrophilic fibers that are shorter than the hydrophobic fibers, the hydrophobic fibers being heat-fused together, at least some of the hydrophilic fibers forming aggregates and dispersing in the sheet, and at least some of the hydrophilic fibers of the aggregates being fused with the surfaces of the hydrophobic fibers, as well as an absorbent article comprising the surface layer.

CITATION LIST

Patent Literature

PTL 1 Japanese Unexamined Patent Publication No. 2002-651

SUMMARY

Problems to be Solved by the Invention

The surface layer described in PTL 1 is an invention whose purpose is to provide an absorbent article wherein large amounts of fluid easily pass through the absorbing layer while small amounts of fluid are easily held in the surface layer, with low potential for producing a damp feel on the skin of the wearer and with a satisfactory feel during wear, the invention being focused primarily on holding fluids, whereas Reference 1 does not contain a description relating to the use of the surface layer as an outer sheet.

It is an object of the present disclosure to provide a nonwoven fabric for an outer sheet of an absorbent article wherein moisture is discharged from a liquid-impermeable sheet while moisture is confined within an outer sheet, so that the wearer is less likely to feel mustiness between the absorbent article and the clothing.

Means for Solving the Problems

The authors of the present disclosure have discovered a nonwoven fabric for an outer sheet of an absorbent article comprising a liquid-impermeable sheet having moisture vapor permeability, the nonwoven fabric having a thickness direction and a planar direction, and a first surface and a second surface, the nonwoven fabric including thermoplastic resin fibers, and cellulosic fibers of which at least a portion form a plurality of fiber masses, the nonwoven fabric comprising a plurality of gaps that are adjacent to first regions of each of the plurality of fiber masses that are facing the first surface, wherein each of the plurality of fiber masses are not joined with the thermoplastic resin fibers.

Effects of the Invention

In the nonwoven fabric for an outer sheet of an absorbent article of the present disclosure, moisture is discharged from a liquid-impermeable sheet while moisture is confined within an outer sheet, so that the wearer is less likely to feel mustiness between the absorbent article and the clothing.

DESCRIPTION OF EMBODIMENTS

Definitions

"Outer Surface" and "Inner Surface"

Figure 1:
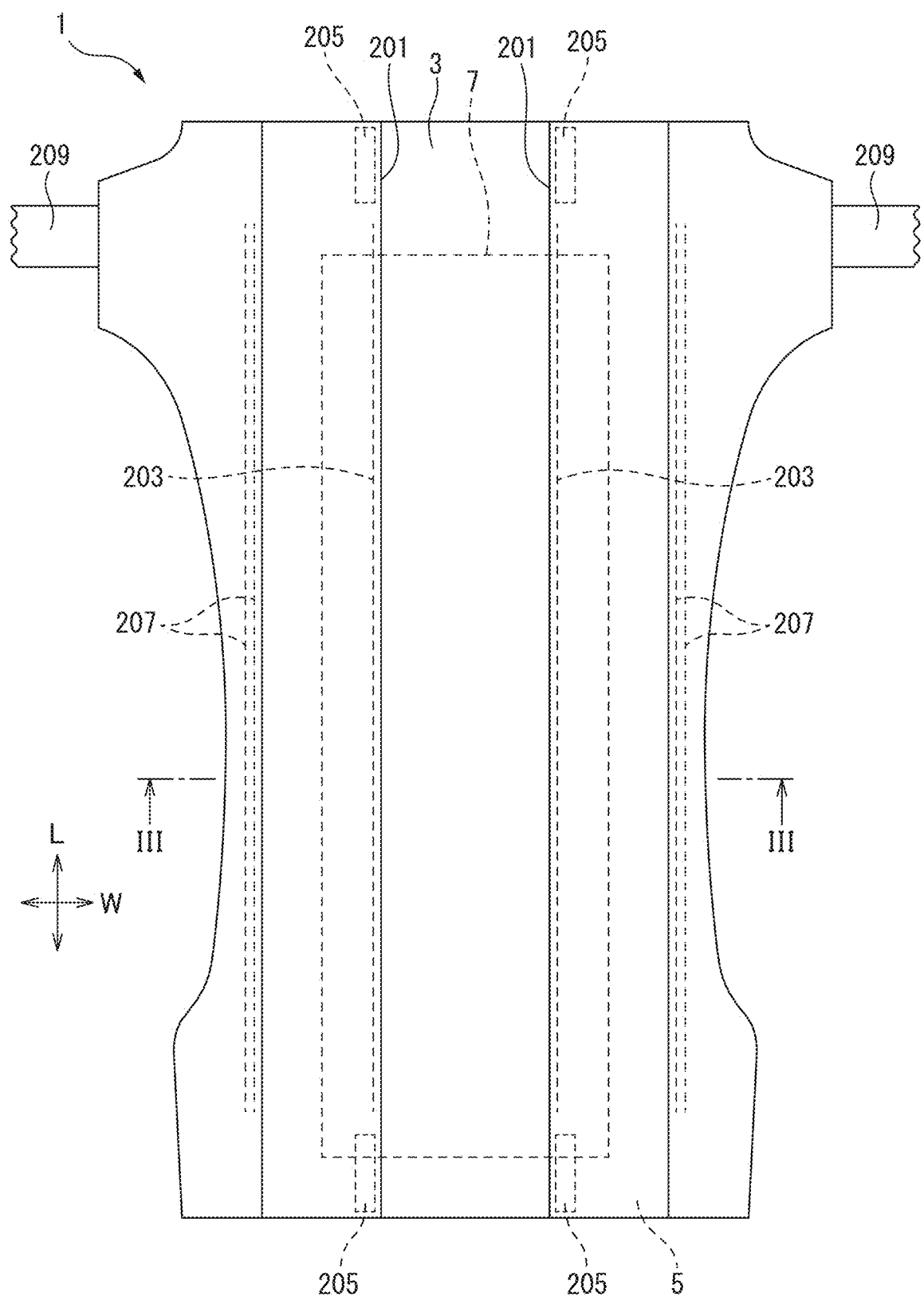
FIG. 1 is an expanded view of the front side of an absorbent article 1 comprising a nonwoven fabric according to a first embodiment as an outer sheet 6.

As used herein, the terms "outer surface" and "inner surface" are terms used for single members, and they mean the surface away from the skin of the wearer and the surface near the skin of the wearer, respectively, when the article is worn.

"Joining" of Fiber Masses and Thermoplastic Resin Fibers

As used herein, the terms "joining" and "joined", as they relate to the fiber masses and thermoplastic resin fibers, mean "fusion" and "fused", respectively. Thus, "each of the plurality of fiber masses are not joined with the thermoplastic resin fibers" means that "each of the plurality of fiber masses are not fused with the thermoplastic resin fibers".

Therefore, "tangling" between the cellulosic fibers composing the fiber masses and the thermoplastic resin fibers and/or cellulosic fibers composing the matrix ("being tangled") is not included in "joining (being joined)", and the nonwoven fabric of the present disclosure may include tangling between the cellulosic fibers composing the fiber masses and the thermoplastic resin fibers and/or cellulosic fibers composing the matrix.

Incidentally, such tangling may be incorporation into the matrix without fusion of the cellulosic fibers composing the fiber masses with the thermoplastic resin fibers and/or cellulosic fibers composing the matrix, or incorporation into the fiber masses without fusion of the thermoplastic resin fibers and/or cellulosic fibers composing the matrix with the cellulosic fibers composing the fiber masses.

"Joining" Between Thermoplastic Resin Fibers

As used herein, the terms "joining" and "joined", as they relate to thermoplastic resin fibers, mean "fusion" and "fused", similar to the fiber masses and thermoplastic resin fibers.

The present disclosure relates to the following aspects.

[Aspect 1]

A nonwoven fabric for an outer sheet of an absorbent article comprising a liquid-impermeable sheet having moisture vapor permeability, the nonwoven fabric having a thickness direction and a planar direction, and a first surface and a second surface, the nonwoven fabric including thermoplastic resin fibers, and cellulosic fibers of which at least a portion form a plurality of fiber masses, the nonwoven fabric comprising a plurality of gaps that are adjacent to first regions of each of the plurality of fiber masses that are facing the first surface, wherein each of the plurality of fiber masses are not joined with the thermoplastic resin fibers.

The nonwoven fabric comprises fiber masses of cellulosic fibers and gaps that are adjacent to first regions of the fiber masses, and therefore moisture that has a tendency to be released from the absorbent body, to pass through the liquid-impermeable sheet having moisture vapor permeability and to be discharged to the outside of the absorbent article when not under pressure, is absorbed and held in a concentrated (spot-like) manner by the fiber masses through the gaps, such that the area of the portions holding the moisture in the planar direction of the nonwoven fabric can be reduced (to spot-like forms). Consequently, even while moisture that has been released from the absorbent body is caused to pass through the liquid-impermeable sheet having moisture vapor permeability and to be discharged, it is possible to reduce the amount of moisture that passes through the nonwoven fabric and is discharged to the outside of the absorbent article.

Even under pressure such as body pressure, since the gaps are compacted preferentially over the fiber masses, the fiber masses absorb and hold moisture that has a tendency to be released from the absorbent body, to pass through the liquid-impermeable sheet having moisture vapor permeability and to be discharged to the outside of the absorbent article, in a concentrated (spot-like) manner through the remaining gaps, such that the area of the portions holding the moisture in the planar direction of the nonwoven fabric can be reduced (to spot-like forms). Even under pressure, therefore, when moisture that has been released from the absorbent body is caused to pass through the liquid-impermeable sheet having moisture vapor permeability and is discharged, it is possible to reduce the amount of moisture that passes through the nonwoven fabric and is discharged to the outside of the absorbent article.

Thus, whether under pressure or not under pressure, the nonwoven fabric will be less likely to discharge moisture gas from the absorbent body to the outside of the absorbent article, and containment of moisture between the absorbent article and the clothing of the wearer, i.e. in the region outside of the absorbent article and inside the clothing of the wearer, can be prevented, so that the wearer will be less likely to experience a sense of mustiness.

When the nonwoven fabric is not under pressure, and fluid is present that has a tendency to be released from the absorbent body, to pass through the liquid-impermeable sheet having moisture vapor permeability and to be discharged to the outside of the absorbent article, the fiber masses of the cellulosic fibers can absorb and hold the fluid. When the outdoor air temperature is low, moisture that has permeated the liquid-impermeable sheet having high moisture vapor permeability condenses on the outer surface of the liquid-impermeable sheet, potentially forming condensed water, but the fiber masses of the cellulosic fibers can absorb and hold the fluid. The fiber masses are not joined with the thermoplastic resin fibers, but rather the fiber masses are able to move in the gaps, primarily in the thickness direction (toward the first surfaces), and therefore the fiber masses are not easily able to maintain a state of contact with the thermoplastic resin fibers for prolonged periods, and fluid held by the fiber masses is transmitted through the thermoplastic resin fibers and migrates to the outer surface of the nonwoven fabric (the outer surface of the outer sheet). Therefore, the nonwoven fabric is less likely to create a feeling of wetness for the wearer on the outer surface of the outer sheet.

In addition, since the gaps are compacted preferentially over the fiber masses when the nonwoven fabric is under pressure, the fiber masses are unlikely to collapse, and the fluid held by the fiber masses is less likely to be extruded out from the fiber masses. In addition, since the fiber masses are not joined with the thermoplastic resin fibers, fluid that has been extruded out from the fiber masses is less likely to migrate through the thermoplastic resin fibers to the outer surface of the nonwoven fabric (the outer surface of the outer sheet).

Consequently, whether under pressure or not under pressure, the nonwoven fabric will be unlikely to cause migration of fluid to the outer surface of the outer sheet, and the wearer will be unlikely to sense a feeling of wetness on the outer surface of the absorbent article.

[Aspect 2]

The nonwoven fabric according to aspect 1, wherein the nonwoven fabric comprises a matrix that includes at least thermoplastic resin fibers, and a plurality of fiber masses dispersed in the matrix.

In this nonwoven fabric, moisture that has a tendency to pass through the nonwoven fabric and to be discharged from the absorbent body to the inside of the absorbent article, can be efficiently absorbed and held by the nonwoven fabric as a whole through the gaps, by the fiber masses dispersed in the matrix that includes thermoplastic resin fibers, allowing moisture that has been released from the absorbent body to pass through the liquid-impermeable sheet having moisture vapor permeability and to be discharged, and allowing reduction in the amount of moisture that passes through the nonwoven fabric and is discharged to the outside of the absorbent article.

[Aspect 3]

The nonwoven fabric according to aspect 1 or 2, wherein outer edges of the gaps in the planar direction are situated further outward than outer edges of the fiber masses in the planar direction.

In this nonwoven fabric, the outer edges of the gaps are further outward than the outer edges of the fiber masses, and the fiber masses can absorb and hold moisture that has a tendency to be released from the absorbent body, to pass through the liquid-impermeable sheet having moisture vapor permeability and to be discharged to the outside of the absorbent article, from the entire first region through the gaps. Consequently, even while moisture that has been released from the absorbent body is caused to pass through the liquid-impermeable sheet having moisture vapor permeability and is discharged, it is possible to reduce the amount of moisture that passes through the nonwoven fabric and is discharged to the outside of the absorbent article.

Moreover, since the outer edges of the gaps in this nonwoven fabric are further outward than the outer edges of the fiber masses, the fiber masses easily move within the gaps in the thickness direction (toward the first surface), and fluid held by the fiber masses is less likely to migrate through the thermoplastic resin fibers to the outer surface of the nonwoven fabric (the outer surface of the outer sheet), whether under pressure or not under pressure.

[Aspect 4]

The nonwoven fabric according to any one of aspects 1 to 3, wherein the nonwoven fabric further comprises gaps adjacent to second regions that face the second surfaces of at least some of the plurality of fiber masses.

Since this nonwoven fabric further comprises gaps adjacent to second regions that face the second surfaces of at least some of the plurality of fiber masses, the fiber masses can absorb and hold moisture that has a tendency to be released from the absorbent body, to pass through the liquid-impermeable sheet having moisture vapor permeability and to be discharged to the outside of the absorbent article when not under pressure, from the first regions and second regions, through the gaps. Consequently, even while moisture that has been released from the absorbent body is caused to pass through the liquid-impermeable sheet having moisture vapor permeability and is discharged, it is possible to reduce the amount of moisture that passes through the nonwoven fabric and is discharged to the outside of the absorbent article.

Moreover, in this nonwoven fabric, although the gaps that are adjacent to the first regions and second regions of the fiber masses are compacted preferentially over the fiber masses when under pressure, they tend to maintain their spaces. Consequently, the nonwoven fabric can absorb and hold moisture that has a tendency to be released from the absorbent body, to pass through the liquid-impermeable sheet having moisture vapor permeability and to be discharged to the outside of the absorbent article, through the gaps that are more likely to be maintained. Consequently, even while moisture that has been released from the absorbent body is caused to pass through the liquid-impermeable sheet having moisture vapor permeability and is discharged, it is possible to reduce the amount of moisture that passes through the nonwoven fabric and is discharged to the outside of the absorbent article.

Moreover, since this nonwoven fabric further comprises gaps adjacent to second regions that face the second surfaces of at least some of the plurality of fiber masses, the fiber masses easily move within the gaps in the thickness direction (toward the first surfaces and second surfaces), and fluid held by the fiber masses is less likely to migrate through the thermoplastic resin fibers to the outer surface of the nonwoven fabric (the outer surface of the outer sheet), whether under pressure or not under pressure.

[Aspect 5]

The nonwoven fabric according to any one of aspects 1 to 4, wherein the thermoplastic resin fibers are joined together.

In this nonwoven fabric, since the thermoplastic resin composing the matrix of the nonwoven fabric is joined together, the gaps formed between the matrix and the fiber masses of the cellulosic fibers easily maintain their shapes, and more easily exhibit the effect described above.

[Aspect 6]

The nonwoven fabric according to any one of aspects 1 to 5, wherein the nonwoven fabric includes the cellulosic fibers in a ratio of 3 to 35 mass %.

Since the nonwoven fabric includes cellulosic fibers in a prescribed ratio, moisture that has a tendency to be released from the absorbent body, to pass through the liquid-impermeable sheet having moisture vapor permeability and to be discharged to the outside of the absorbent article, is easily absorbed and held in a concentrated (spot-like) manner through the gaps, by the fiber masses of cellulosic fibers, and the area of the portions holding the moisture in the planar direction of the nonwoven fabric can be reduced (to spot-like forms). Consequently, even while moisture that has been released from the absorbent body is caused to pass through the liquid-impermeable sheet having moisture vapor permeability and is discharged, it is possible to reduce the amount of moisture that passes through the nonwoven fabric and is discharged to the outside of the absorbent article.

[Aspect 7]

The nonwoven fabric according to any one of aspects 1 to 6, wherein the cellulosic fibers have a shorter mean fiber length than the thermoplastic resin fibers.

In this nonwoven fabric, since the cellulosic fibers have shorter fiber lengths than the thermoplastic resin fibers, the fiber masses of cellulosic fibers in the nonwoven fabric separate from the matrix of thermoplastic resin fibers, tending to be situated in a dispersed state in the matrix, and tending to more easily exhibit the effect described above.

[Aspect 8]

The nonwoven fabric according to any one of aspects 1 to 7, wherein the cellulosic fibers include organic cotton.

Since the cellulosic fibers in this nonwoven fabric include organic cotton, the user is more likely to experience a feeling of assurance. Moreover, since the cellulosic fibers in this nonwoven fabric include organic cotton, the cellulosic fibers tend to have shorter fiber lengths than the thermoplastic resin fibers, and the nonwoven fabric tends to more easily exhibit the effect described above.

[Aspect 9]

The nonwoven fabric according to any one of aspects 1 to 8, wherein the cellulosic fibers include hirsutum cotton.

Since the cellulosic fibers in this nonwoven fabric include hirsutum cotton, the user is more likely to experience a feeling of assurance. Moreover, since the cellulosic fibers in this nonwoven fabric include hirsutum cotton, the cellulosic fibers tend to have shorter fiber lengths than the thermoplastic resin fibers, and the nonwoven fabric tends to easily exhibit the effect described above.

[Aspect 10]

The nonwoven fabric according to any one of aspects 1 to 9, wherein the nonwoven fabric has a multilayer structure including a clothing side layer with a clothing-contacting surface, and the nonwoven fabric comprises the plurality of fiber masses in a layer other than the clothing side layer.

Since the fiber masses in this nonwoven fabric are situated in a layer of the nonwoven fabric other than the clothing side layer, the fiber masses of the cellulosic fibers are unlikely to be shed during use. Moreover, since the fiber masses in this nonwoven fabric are situated in a layer of the nonwoven fabric other than the clothing side layer, fluid that is absorbed and held in the fiber masses of the cellulosic fibers is unlikely to contact with the wearer, and the wearer is unlikely to experience discomfort.

[Aspect 11]

The nonwoven fabric according to any one of aspects 1 to 10, wherein the nonwoven fabric comprises a plurality of protrusions protruding in a direction from the first surface toward the second surface, and a plurality of depressions that are depressed in a direction from the second surface toward the first surface, each of the plurality of protrusions and each of the plurality of depressions overlapping in the thickness direction.

Since the nonwoven fabric has a plurality of depressions that are depressed on the second surface, when it is used as an outer sheet, separated regions are formed between the depressions of the second surface and the liquid-impermeable sheet. Thus, since moisture that has a tendency to be released from the absorbent body, to pass through the liquid-impermeable sheet having moisture vapor permeability and to be discharged to the outside of the absorbent article, is absorbed and held by the cellulosic fibers, and especially the fiber masses, of the nonwoven fabric, while being retained as a state of moisture in the gaps adjacent to the fiber masses, and in the separated regions (that is, since the gaps and separated regions are in a highly moist state), a gas-liquid equilibrium state is formed between the moisture in the separated regions (gas phase) and fluid absorbed and held in the absorbent body (liquid phase), and any further release of moisture from the absorbent body is inhibited. Consequently, the wearer is unlikely to feel mustiness in the regions on the outside of the absorbent article and the inside of clothing.

[Aspect 12]

The nonwoven fabric according to aspect 11, wherein each of the plurality of protrusions forms a ridge running in one direction, the nonwoven fabric comprises a plurality of furrows having the furrow bottoms between adjacent ridges, and each of the plurality of furrows comprises a plurality of recesses, depressed in a direction from the first surface toward the second surface, which are arranged intermittently in one direction on the furrow bottoms, each of them having a bottom part.

This nonwoven fabric, when used as an outer sheet, can form separated regions between the outer sheet and the liquid-impermeable sheet. Specifically, this nonwoven fabric, when used as a liquid-permeable sheet, can form separated regions between the depressions of the outer sheet, and the absorbent body. In addition, even when the nonwoven fabric has temporarily collapsed under pressure and the separated regions have temporarily collapsed with it, the nonwoven fabric easily returns to its original form and the separated regions are easily restored, when not under pressure. Consequently, the nonwoven fabric is unlikely to produce a feeling of mustiness for the wearer in the region outside of the absorbent article and the inside of clothing, for a longer period of time than the nonwoven fabric of aspect 11.

[Aspect 13]

An absorbent article including a liquid-permeable sheet, a liquid-impermeable sheet, an absorbent body and an outer sheet, in that order, wherein the outer sheet is the nonwoven fabric according to any one of aspects 1 to 12.

The absorbent article has the effect described above.

[Aspect 14]

The absorbent article according to aspect 12, wherein the second surface of the nonwoven fabric constitutes outer surface of the outer sheet.

In this absorbent article, the first surface of the nonwoven fabric constitutes the inner surface of the outer sheet, and therefore the gaps are situated on the first surface side of the fiber masses, i.e. on the liquid-impermeable sheet side. Consequently, whether under pressure or not under pressure, moisture that has a tendency to be released from the absorbent body, to pass through the liquid-impermeable sheet having moisture vapor permeability and to be discharged to the outside of the absorbent article can be absorbed and held by the fiber masses in a concentrated (spot-like) manner through the gaps present on the liquid-impermeable sheet side, and it is possible to cause moisture that has been released from the absorbent body to pass through the liquid-impermeable sheet having moisture vapor permeability and to be discharged, and to thereby reduce the amount of moisture passing through the nonwoven fabric and being discharged to the outside of the absorbent article.

[Aspect 15]

The absorbent article according to aspect 13 or 14, wherein the liquid-permeable sheet is a nonwoven fabric according to any one of aspects 1 to 12.

Since the liquid-permeable sheet and outer sheet in this absorbent article are nonwoven fabrics as mentioned above, moisture that has been discharged from the absorbent body is less able to be discharged not only to the outside of the absorbent article but also to the inside of the absorbent article, and therefore the wearer is unlikely to sense a feel of mustiness in either the regions on the outside of the absorbent article and the inside of the clothing, or in the region on the inside of the absorbent article.

The nonwoven fabric for an outer sheet of an absorbent article according to the present disclosure will now be described in greater detail, assuming that the nonwoven fabric is in a state of being used as an outer sheet of an absorbent article.

Figure 2:
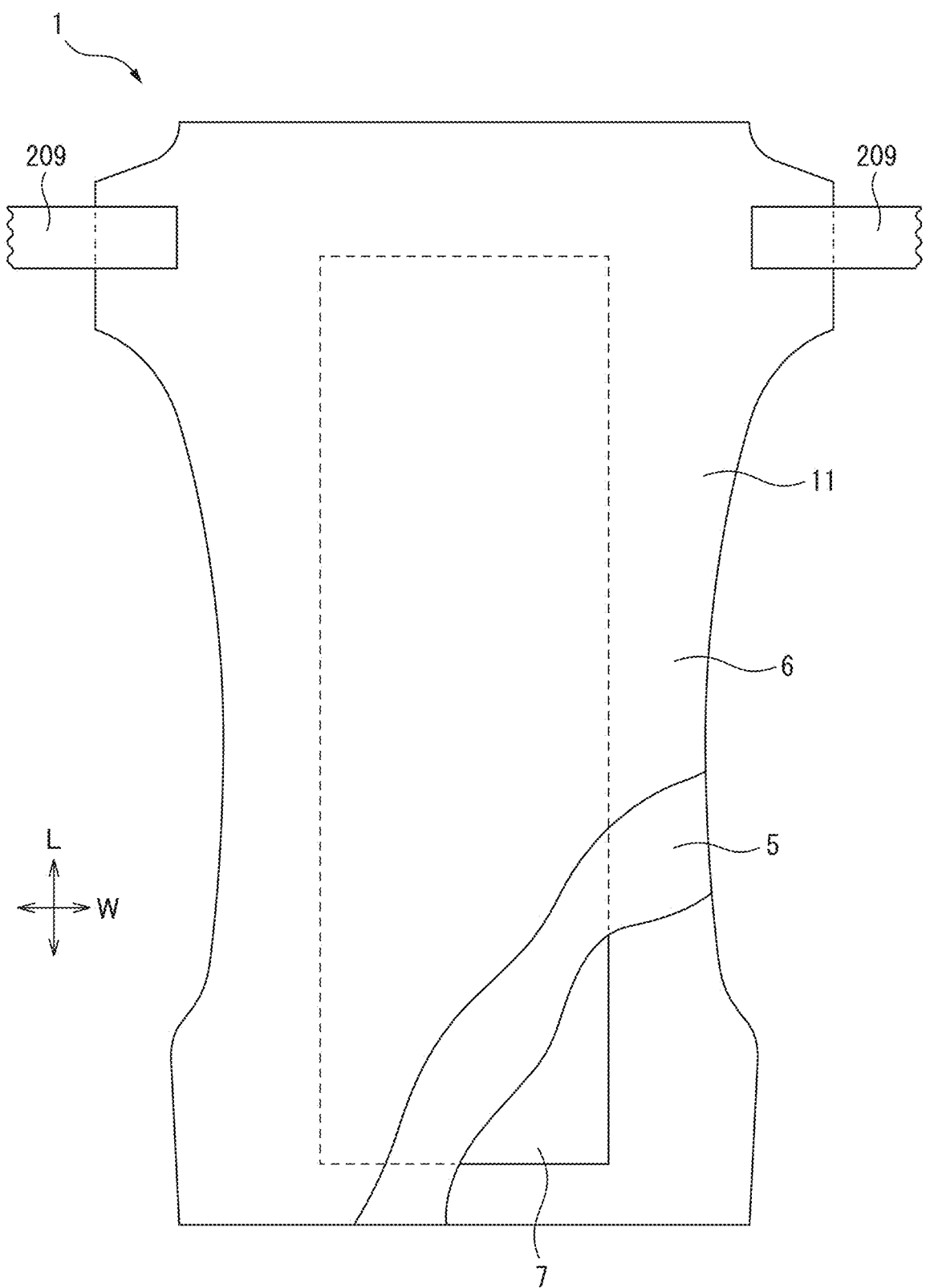
FIG. 2 is an expanded view of the back side of the absorbent article 1 comprising a nonwoven fabric according to the first embodiment as the outer sheet 6.
Figure 3:
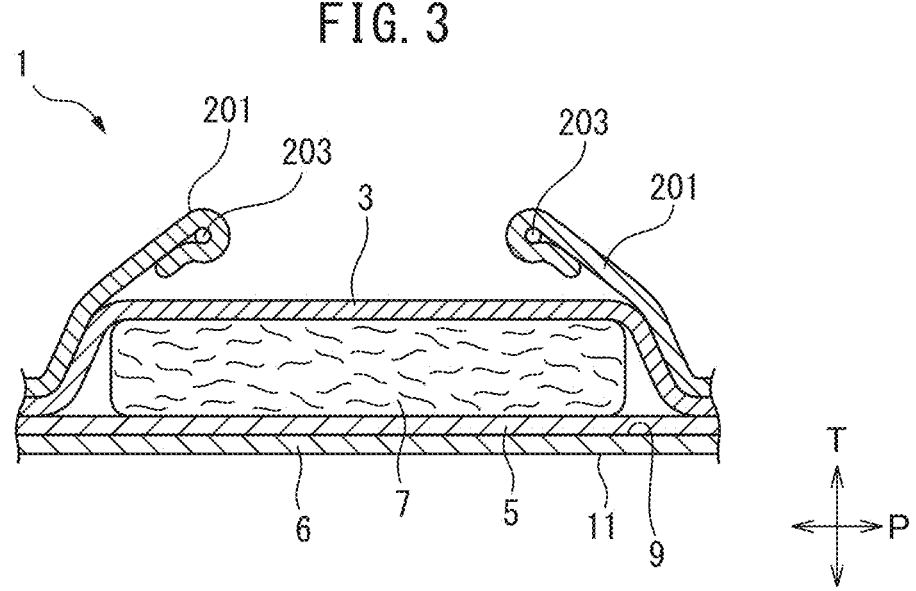
FIG. 3 is a partial end view along edge III-III of FIG. 1.
Figure 4:
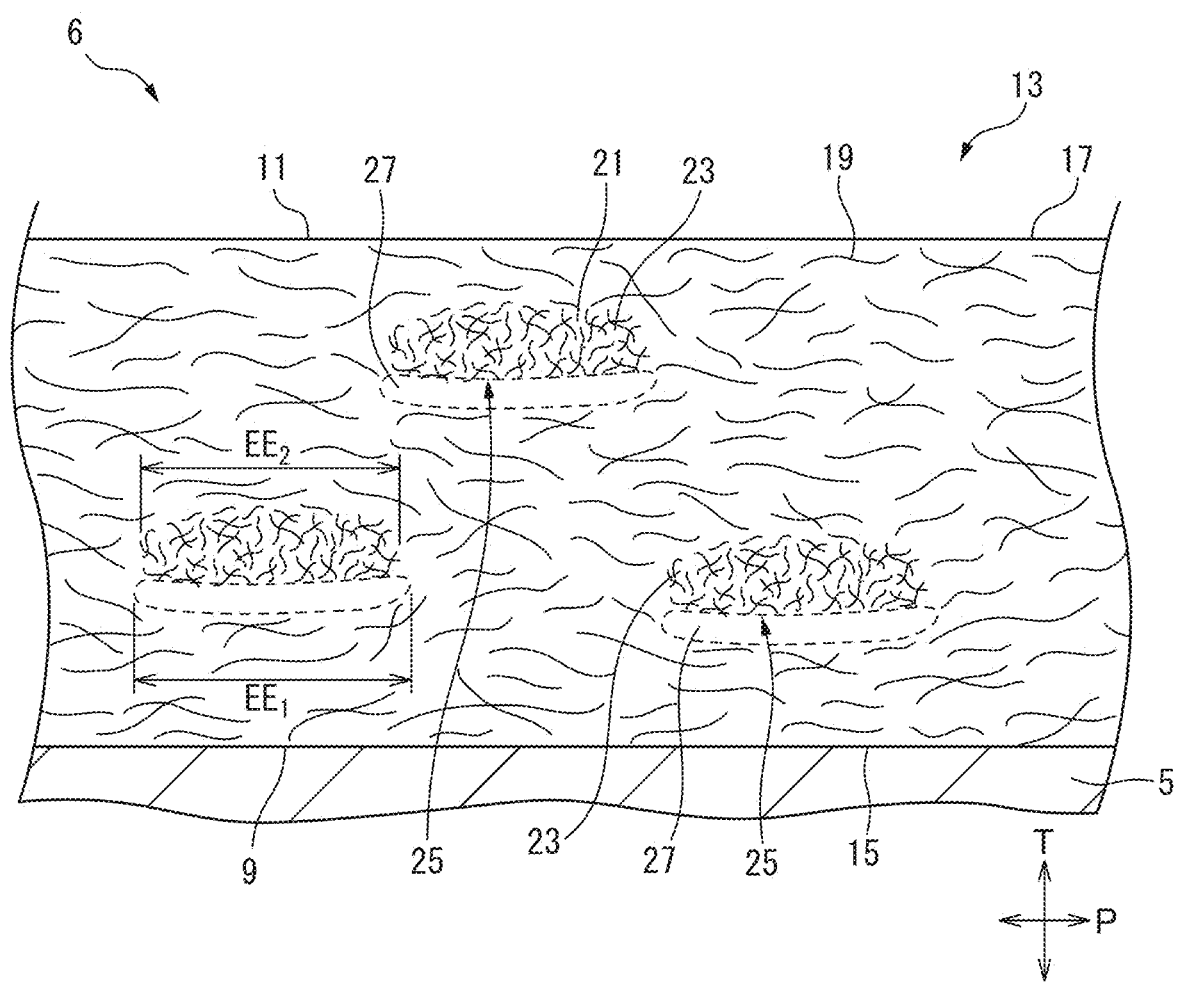
FIG. 4 is a partial magnified view of the outer sheet 6 of FIG. 3.

FIG. 1 is an expanded view of an absorbent article 1, and specifically a tape-type disposable diaper, in which a nonwoven fabric according to an embodiment (first embodiment) of the present disclosure is included as the outer sheet 6. FIG. 2 is a rear view of the absorbent article 1 including a nonwoven fabric according to the first embodiment as the outer sheet 6. FIG. 3 is a partial end view along edge III-III of FIG. 1. FIG. 4 is a partial magnified view of the region near the outer sheet 6 of FIG. 3. FIG. 4 is a diagram schematically illustrating the relationship between the thermoplastic resin fibers 19, fiber masses 23 of the cellulosic fibers 21 and gaps 27 in the outer sheet 6 (nonwoven fabric 13), which however is not intended as a limitative interpretation of the present disclosure.

According to the first embodiment, the absorbent article 1 comprises a liquid-permeable sheet 3, a liquid-impermeable sheet 5, an absorbent body 7 and the outer sheet 6, in that order. The absorbent article 1 has a lengthwise direction L and a widthwise direction W.

Incidentally, according to the first embodiment, the absorbent article 1 has a pair of anti-leakage walls 201 including an elastic member 203, an anchoring part 205 for anchoring of the anti-leakage walls 201 to the liquid-permeable sheet 3, an elastic member 207 and a tape fastener 209, as shown in FIG. 1, but because these are known in the technical field they will not be explained here.

According to the first embodiment, the outer sheet 6 includes a skin side surface 9 located on the wearer skin side, and a clothing-contacting surface 11 which is the surface that is on the side opposite the skin side surface 9 and that contacts with the clothing of the wearer. The skin side surface 9 of the outer sheet 6 is joined to the liquid-impermeable sheet 5.

As shown in FIG. 4, the nonwoven fabric 13 composing the outer sheet 6 has a thickness direction T and a planar direction P, and a first surface 15 and second surface 17, the first surface 15 forming the skin side surface 9 of the outer sheet 6 and the second surface 17 forming the clothing-contacting surface 11 of the outer sheet 6. For the purpose of illustration, FIG. 4 is shown with the up-down direction inverted with respect to FIG. 3, or in other words, it is shown with the outer sheet 6 on the upper side and the liquid-impermeable sheet 5 on the lower side.

The nonwoven fabric 13 includes thermoplastic resin fibers 19 and cellulosic fibers 21, the cellulosic fibers 21 forming a plurality of fiber masses 23 and the plurality of fiber masses 23 being disposed across spacings in the matrix of the thermoplastic resin fibers 19, or in other words, the plurality of fiber masses 23 being dispersed in the matrix of the thermoplastic resin fibers 19.

The nonwoven fabric 13 also comprises a plurality of gaps 27 adjacent to the first regions 25 of the plurality of fiber masses 23 that are facing the first surface 15.

The fiber masses 23, and specifically the cellulosic fibers 21 composing the fiber masses 23, are not joined to the thermoplastic resin fibers 19 composing the matrix.

As shown in FIG. 4, in the nonwoven fabric 13, the outer edges $EE_1$ of the gaps 27 in the planar direction P are situated further outward than the outer edges $EE_2$ of the fiber masses 23 in the planar direction P. Thus, the fiber masses 23 can absorb and hold moisture that has a tendency to be released from the absorbent body 7, to pass through the liquid-impermeable sheet having moisture vapor permeability 5 and to be discharged to the outside of the absorbent article 1, from the entire first regions 25 through the gaps 27. Consequently, even while moisture that has been released from the absorbent body 7 is caused to pass through the liquid-impermeable sheet having moisture vapor permeability 5 and is discharged, it is possible to reduce the amount of moisture that passes through the nonwoven fabric 13 and is discharged to the outside of the absorbent article 1.

Moreover, since the outer edges $EE_1$ of the gaps 27 in the nonwoven fabric 13 are further outward than the outer edges $EE_2$ of the fiber masses 23, the fiber masses 23 easily move within the gaps 27 in the thickness direction T (toward the first surface 15), and fluid held by the fiber masses 23 is unlikely to migrate through the thermoplastic resin fibers 19 to the outer surface of the nonwoven fabric 13 (the outer surface of the outer sheet 6), whether under pressure or not under pressure.

Figure 5:
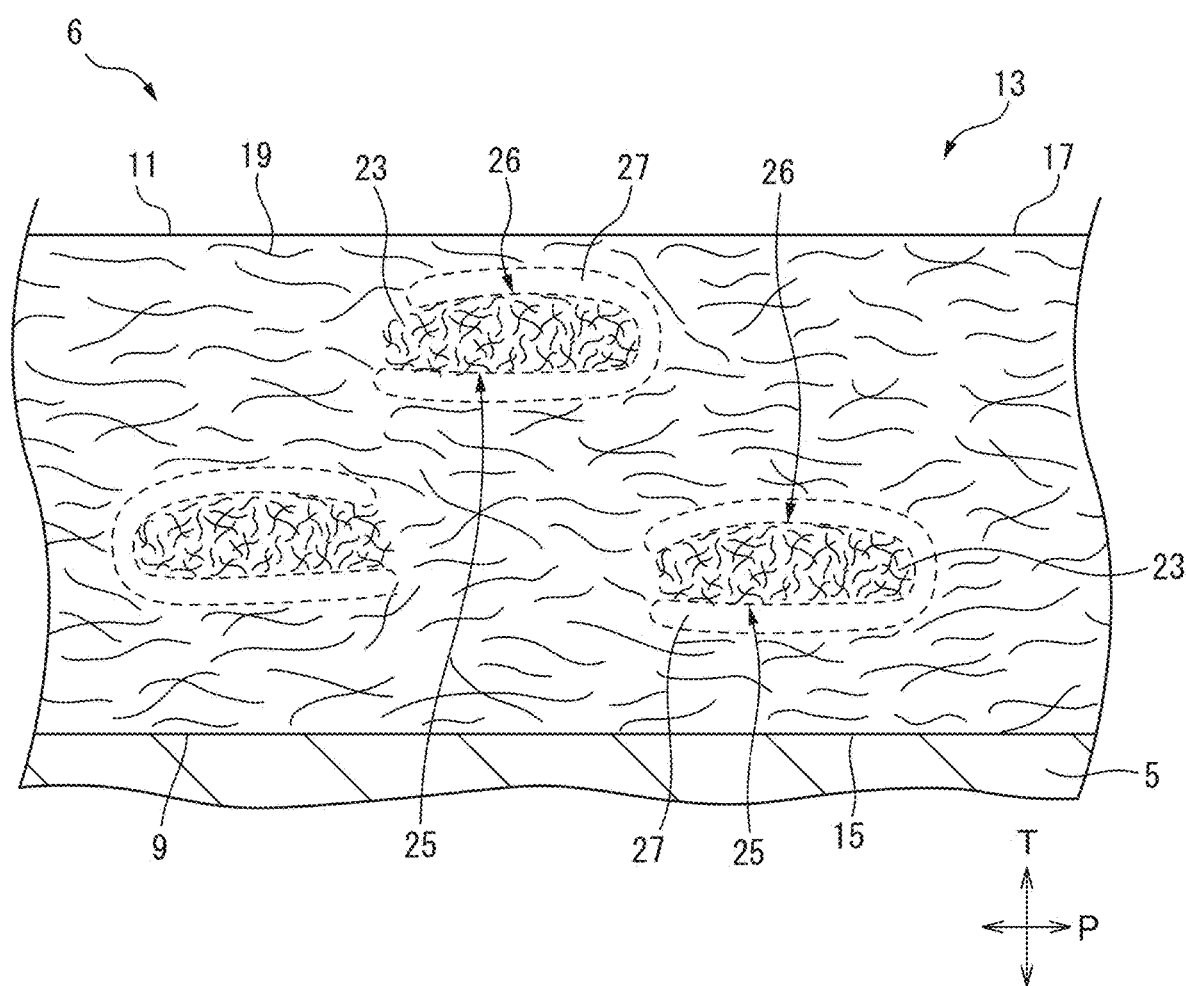
FIG. 5 is a diagram illustrating a nonwoven fabric 13 according to another embodiment (second embodiment) of the present disclosure.

FIG. 5 is a diagram illustrating a nonwoven fabric 13 according to another embodiment (second embodiment) of the present disclosure, being an end view corresponding to FIG. 4. FIG. 5, like FIG. 4, is a diagram schematically illustrating the relationship between the thermoplastic resin fibers 19, the fiber masses 23 of the cellulosic fibers 21 and the gaps 27, which however is not intended as a limitative interpretation of the present disclosure.

The nonwoven fabric 13 according to the second embodiment further comprises gaps 27 adjacent to the second regions 26 of each of the plurality of fiber masses 23 that are facing the second surface 17 of the nonwoven fabric 13. Specifically, the gaps 27 adjacent to the first regions 25, and the gaps 27 adjacent to the second regions 26 are connected at the individual fiber masses 23. Explanation of the other sections will be omitted since they are similar to the nonwoven fabric of the first embodiment.

According to the first embodiment and second embodiment, the nonwoven fabric 13 has a single-layer structure, but the nonwoven fabric of the present disclosure may instead have a multilayer structure, such as a two-layer structure with a clothing side layer having a clothing-contacting surface, and a skin side layer disposed further to the skin side than the clothing side layer, or a three-layer structure with a clothing side layer having a clothing-contacting surface, a skin side layer disposed further to the skin side than the clothing side layer, and an intermediate layer between them. Such nonwoven fabrics include those wherein the nonwoven fabric itself has a multilayer structure, and those wherein the web has been formed with a multilayer structure prior to formation of the nonwoven fabric.

In such an embodiment, the fiber masses of the cellulosic fibers are preferably not included in the clothing side layer, but are included in a layer other than the clothing side layer. Specifically, when the nonwoven fabric of the present disclosure has a two-layer structure with a clothing side layer and a skin side layer, the fiber masses of the cellulosic fibers preferably are not included in the clothing side layer but rather are included in the skin side layer. When the nonwoven fabric of the present disclosure has a three-layer structure with a clothing side layer, intermediate layer and skin side layer, the fiber masses of the cellulosic fibers preferably are not included in the clothing side layer but rather are included in the intermediate layer and/or skin side layer.

This is from the viewpoint of minimizing shedding of the fiber masses from the nonwoven fabric. Moreover, since fluid absorbed and held in the fiber masses of the cellulosic fibers are unlikely to contact with the wearer on the outer surface of the absorbent body, it is unlikely to cause the wearer to perceive a condition of dampness, and unlikely to create discomfort for the wearer. Furthermore, since the clothing side layer of the nonwoven fabric of the present disclosure does not contain cellulosic fibers, it is possible to prevent impairment of the feel on the skin or reduction in flexibility due to cellulosic fibers, such as cotton, and the nonwoven fabric of the present disclosure can exhibit an excellent feel on the skin, and flexibility.

According to the first embodiment and second embodiment, the nonwoven fabric 13 is a flat nonwoven fabric wherein both the first surface 15 and the second surface 17 are flat, but the nonwoven fabric of the present disclosure may also be a shaped nonwoven fabric having a shaped structure.

As an embodiment wherein the nonwoven fabric of the present disclosure is a shaped nonwoven fabric having a shaped structure, the nonwoven fabric comprises a plurality of protrusions protruding in a direction from the first surface toward the second surface (protruding at the second surface), and a plurality of depressions that are depressed in a direction from the second surface toward the first surface (depressed at the first surface), each of the plurality of protrusions and each of the plurality of depressions overlapping in the thickness direction of the nonwoven fabric. Thus, when the liquid-impermeable sheet is disposed on the second surface side (when the second surface of the shaped nonwoven fabric is joined with the liquid-impermeable sheet), the depressions can form the aforementioned separated regions between themselves and the absorbent body.

FIG. 6 to FIG. 10 are diagrams illustrating a shaped nonwoven fabric 113 according to another embodiment (third embodiment) of the present disclosure, and an absorbent article 101 including the shaped nonwoven fabric 113 as an outer sheet 106.

Figure 6:
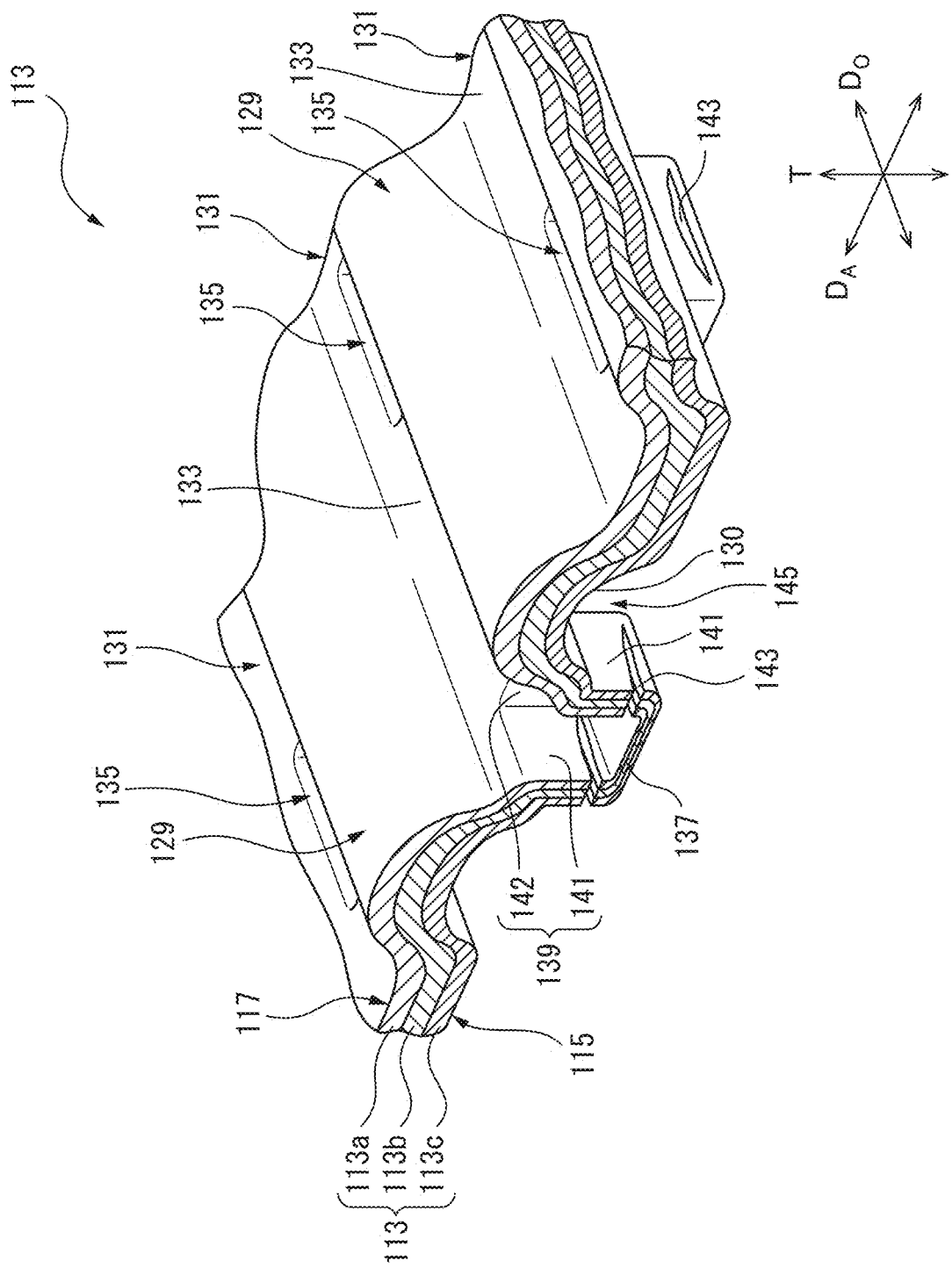
FIG. 6 is a perspective view of a shaped nonwoven fabric 113, according to a third embodiment.
Figure 7:
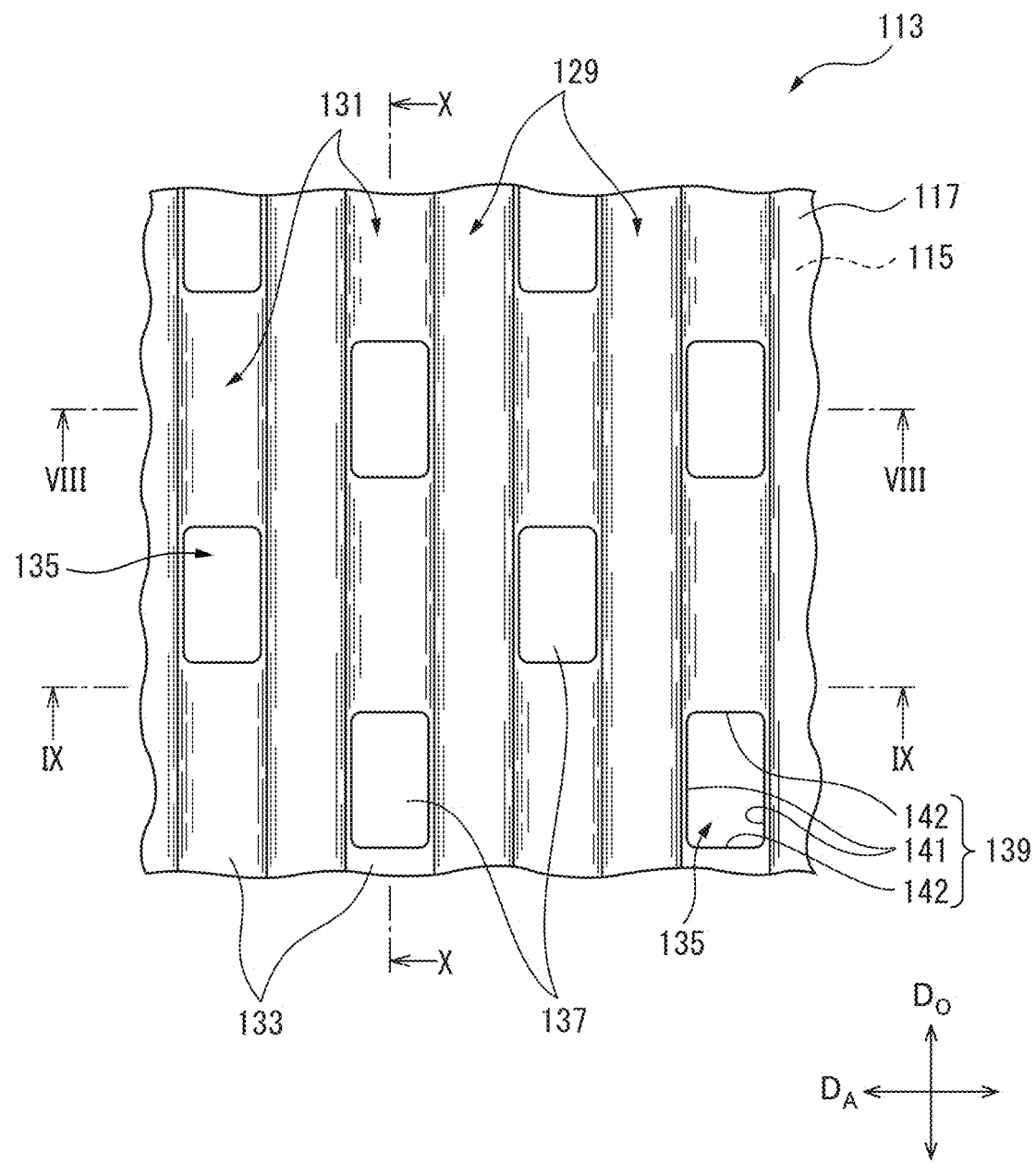
FIG. 7 is a plan view of the shaped nonwoven fabric 113.
Figure 8:
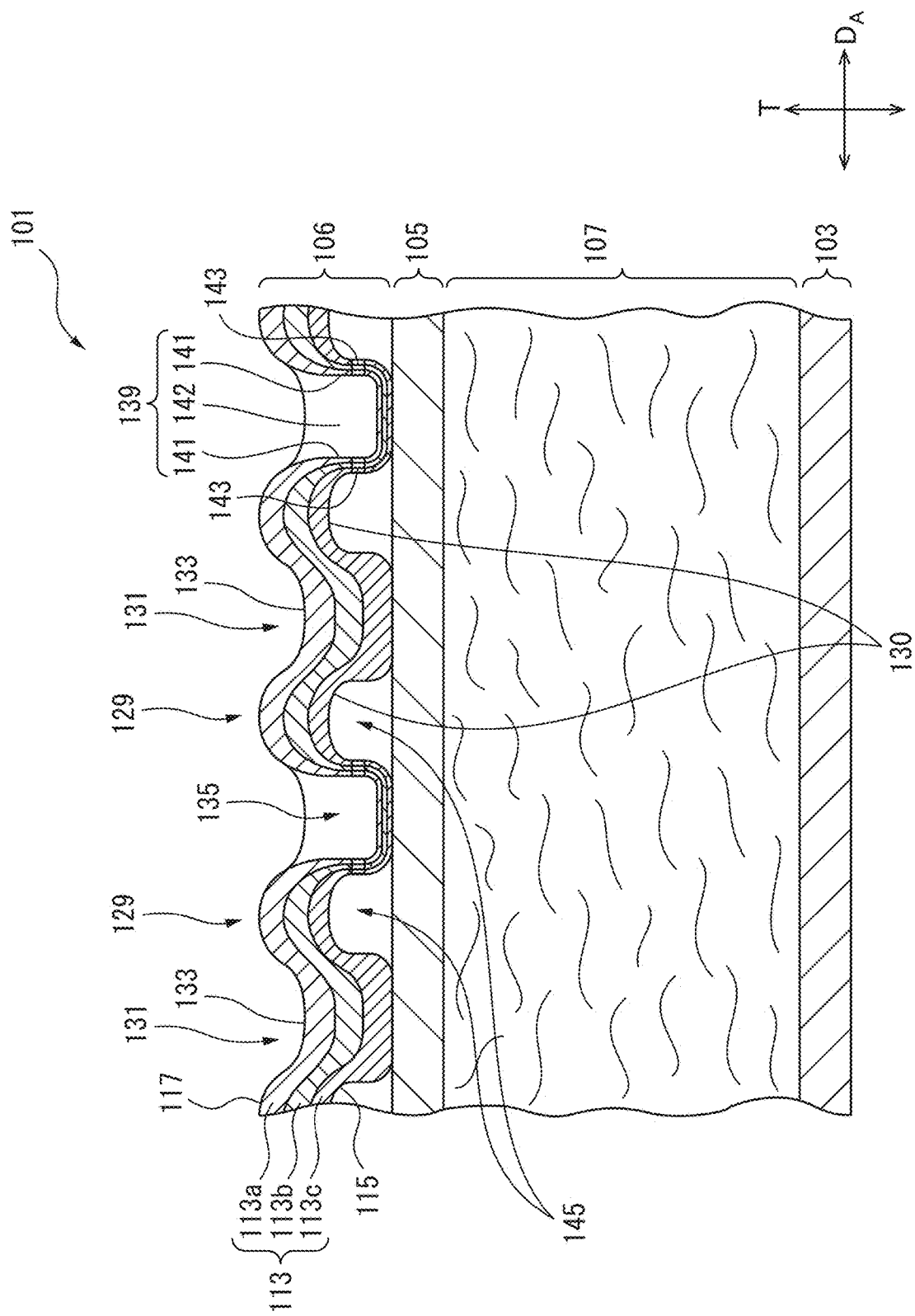
FIG. 8 is a cross-sectional view along cross-section VIII-VIII of FIG. 7.
Figure 9:
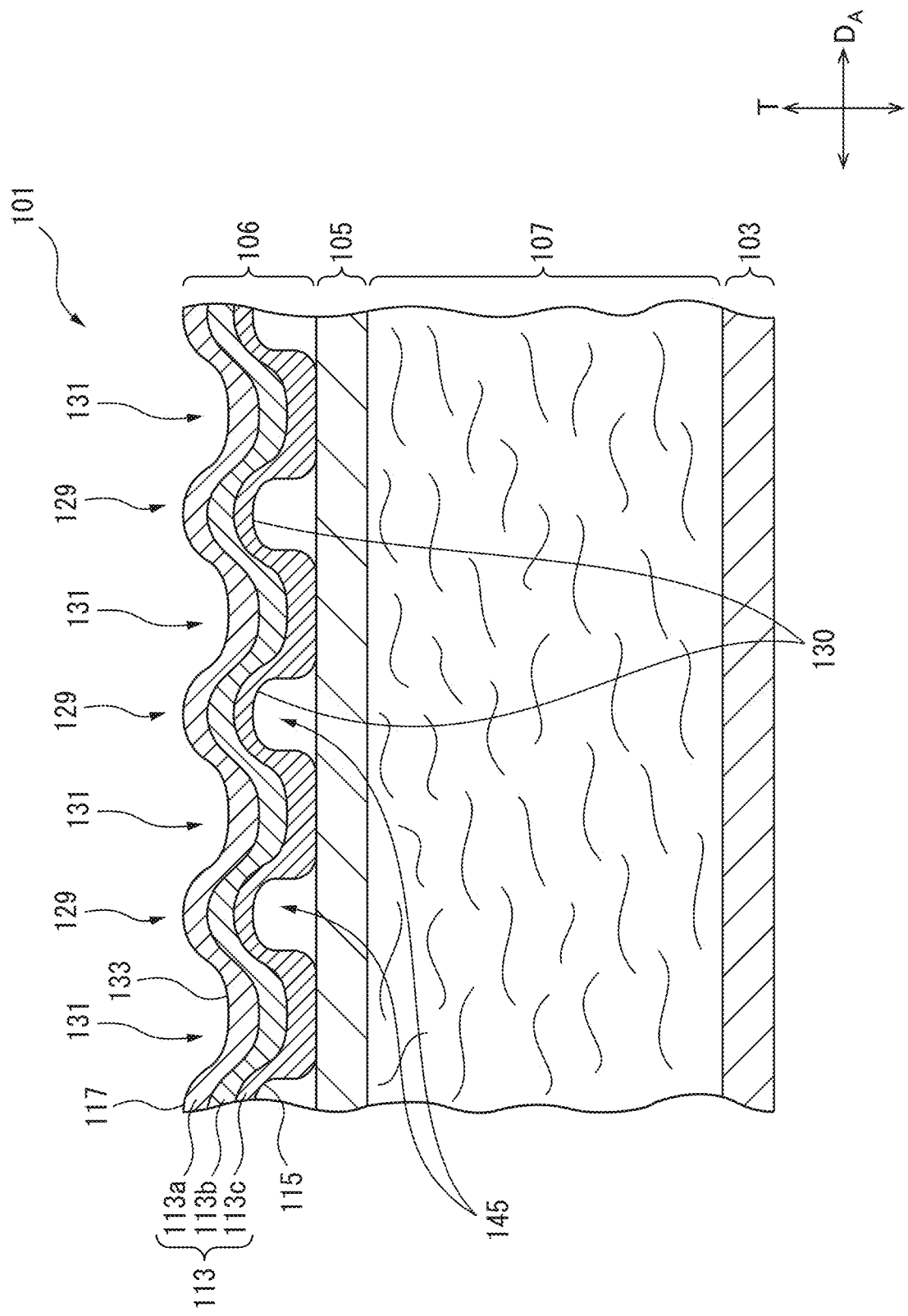
FIG. 9 is a cross-sectional view along cross-section IX-IX of FIG. 7.
Figure 10:
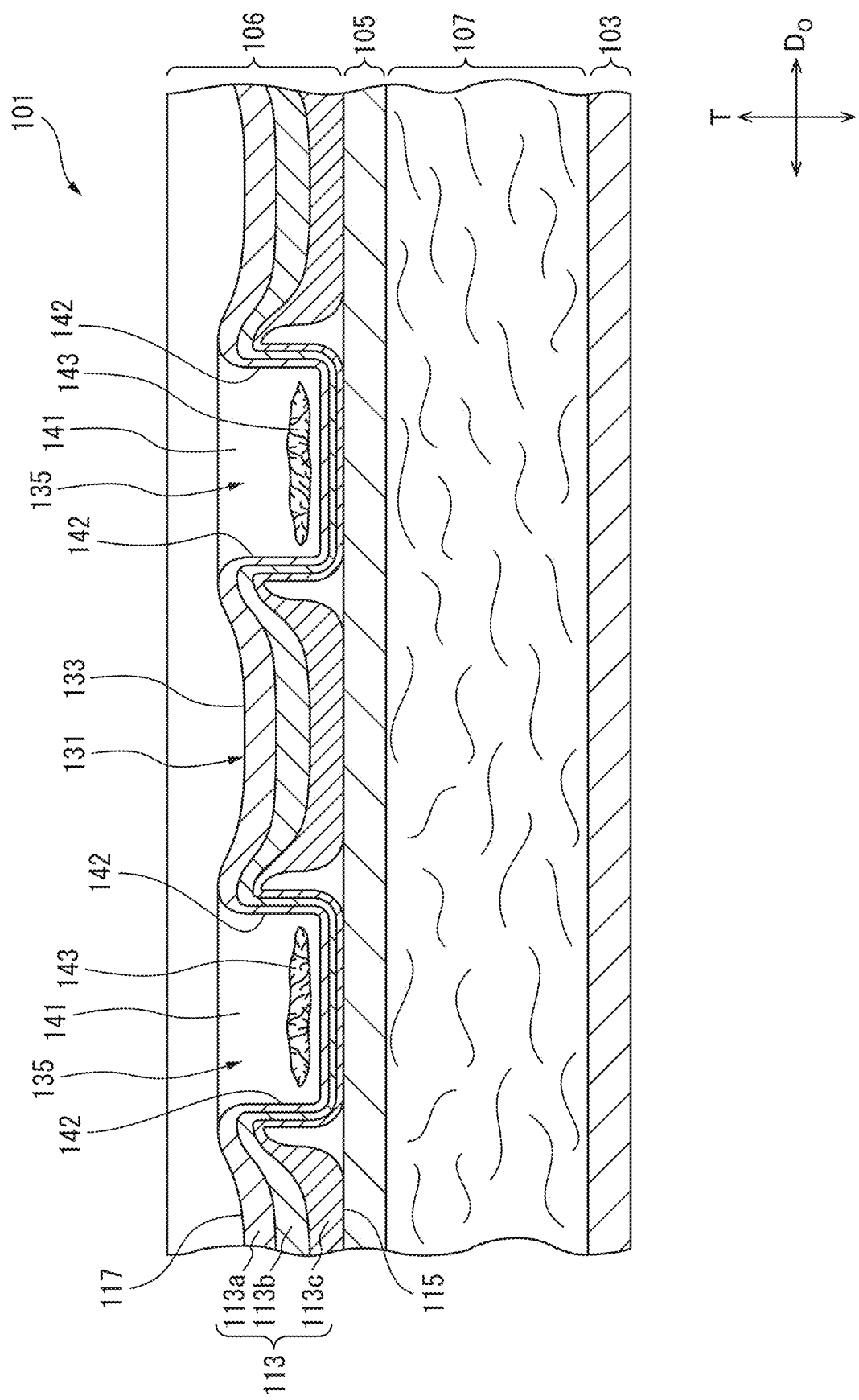
FIG. 10 is a cross-sectional view along cross-section X-X of FIG. 7.

Specifically, FIG. 6 is a perspective view of a shaped nonwoven fabric 113, according to a third embodiment. FIG. 7 is a plan view of the shaped nonwoven fabric 113. FIG. 8 is a cross-sectional view along cross-section VIII-VIII of FIG. 7. FIG. 9 is a cross-sectional view along cross-section IX-IX of FIG. 7. FIG. 10 is a cross-sectional view along cross-section X-X of FIG. 7. Incidentally, a shaped nonwoven fabric 113 is shown in FIG. 6 and FIG. 7, and an absorbent article 101 is shown in FIG. 8 to FIG. 10. FIG. 8 to FIG. 10 are shown with the outer sheet 106 on the upper side.

The shaped nonwoven fabric 113 has a three-layer structure with a clothing side layer 113a having a clothing-contacting surface, a skin side layer 113c, and an intermediate layer 113b between the clothing side layer 113a and skin side layer 113c. The clothing side layer 113a is formed from thermoplastic resin fibers, and both the intermediate layer 113b and the skin side layer 113c include thermoplastic resin fibers and cellulosic fibers, of which at least a portion form a plurality of fiber masses.

The shaped nonwoven fabric 113 has, in the absorbent article 101, a first surface 115 constituting the surface on the liquid-impermeable sheet 105 side, and a second surface 117 constituting the clothing-contacting surface.

In the shaped nonwoven fabric 113, each of the plurality of protrusions protrudes in a direction from the first surface 115 toward the second surface 117, forming a ridge 129 that extends in one direction $D_O$. Also, the shaped nonwoven fabric 113 comprises, along the ridges 129, a plurality of depressions 130 that are depressed 117 in a direction from the second surface toward the first surface 115. Each of the plurality of ridges 129 and the plurality of depressions 130 overlap in the thickness direction T of the shaped nonwoven fabric 113.

The shaped nonwoven fabric 113 comprises a plurality of furrows 131 between two ridges 129 adjacent to the other direction $D_A$ that is perpendicular to the one direction $D_O$, each of them having a furrow bottom 133. Each of the plurality of furrows 131 comprises a plurality of recesses 135 arranged intermittently in one direction $D_O$ on the furrow bottom 133, and depressed in a direction from the second surface toward the first surface, each having a bottom part 137.

Each of the plurality of recesses 135 is composed of a bottom part 137, and a perimeter wall section 139 connecting the furrow bottom 133 and the bottom part 137. The perimeter wall section 139 is partitioned into a pair of first perimeter wall sections 141 aligned along the one direction $D_O$, and a pair of second perimeter wall sections 142 aligned along the other direction $D_A$.

Each of the pair of first perimeter wall sections 141 aligned along the one direction $D_O$ comprises a hole 143 running through from the first surface 115 to the second surface 117.

For each of the plurality of recesses 135, the bottom part 137 has the highest fiber density of the shaped nonwoven fabric 113. Thus, in cases of low outdoor air temperature, for example, moisture that has passed through the liquid-impermeable sheet having high moisture vapor permeability 105 condenses on the outer surface of the liquid-impermeable sheet 105, sometimes forming condensed water, but the condensed water is captured in the bottom parts 137 which have high fiber density, and the condensed water pools in the bottom parts 137 of the outer sheet 106 (shaped nonwoven fabric 113) are unlikely to be discharged to the outside of the absorbent article.

The outer sheet 106 (shaped nonwoven fabric 113) has separated regions 145 between it and the liquid-impermeable sheet 105. Specifically, the outer sheet 106 (shaped nonwoven fabric 113) has separated regions 145 between the depressions 130 and the absorbent body 107.

Consequently, when fluid absorbed and held in the absorbent body 107 has passed through the liquid-impermeable sheet having moisture vapor permeability 105 from the absorbent body 107 in the form of moisture such as evaporation, and is discharged into the outer sheet 106, the cellulosic fibers in the intermediate layer 113b and skin side layer 113c of the outer sheet 106 (shaped nonwoven fabric 113) (not shown) absorb and hold the moisture, while retaining it in the separated regions 145 in the state of moisture (that is, the separated regions 145 are in a highly humid state), and therefore a gas-liquid equilibrium state is formed between the moisture (gas phase) in the separated regions 145 and the fluid (liquid phase) absorbed and held in the absorbent body 107, discharge of moisture from the outer sheet 106 to the outside does not occur even though moisture is caused to pass from the absorbent body 107 through the liquid-impermeable sheet having moisture vapor permeability 105 and is discharged, and it is possible to prevent containment of moisture in the regions of the outside of the absorbent article 101 and the inside of the clothing of the wearer. The wearer is therefore unlikely to experience mustiness.

In the outer sheet 106 (shaped nonwoven fabric 113), the depressions 130 are not joined to the liquid-impermeable sheet 105, and the portions of the furrows 131 on the first surface 115 side are joined to the liquid-impermeable sheet 105 by an adhesive (not shown). In the shaped nonwoven fabric 113, the portions of the furrows 131 on the first surface 115 sides of the furrow bottoms 133 are also joined to the liquid-impermeable sheet 105 by an adhesive (not shown).

The outer sheet 106 (shaped nonwoven fabric 113) has a curved shape that protrudes to the second surface 117 side at the ridges 129, and has a curved shape that protrudes to the first surface 115 side at the furrows 131. In other words, the shaped nonwoven fabric has an essentially wavy cross-section in which concavoconvexities alternatingly repeat in the other direction $D_A$.

According to an embodiment in which the nonwoven fabric of the present disclosure is a shaped nonwoven fabric, the shaped structure may have not only overlapping regions which are overlapping with the absorbent body in the thickness direction of the absorbent article, but also non-overlapping regions which are not overlapping with the absorbent body in the thickness direction of the absorbent article. This will allow moisture discharged from the side edges of the absorbent body to be confined to the separated regions between the liquid-impermeable sheet and the shaped nonwoven fabric.

The pitch of the ridges 129 in the other direction $D_A$ is preferably 0.25 to 5.0 mm, more preferably 0.5 to 3.0 mm and even more preferably 0.75 to 2.0 mm. If the pitch is less than 0.25 mm, the shaped structure of the shaped nonwoven fabric will be too fine, it may not be possible to significantly reduce the contact area between the shaped nonwoven fabric and the skin of the wearer, and the feel on the skin of the shaped nonwoven fabric may be reduced. If the pitch exceeds 5.0 mm, it will be difficult to obtain a flexible feel on the skin by means of the shaped structure.

The height from the furrow bottoms 133 of the furrows 131 to the top sections of the ridges 129 (the height in the thickness direction T of the nonwoven fabric) is preferably 0.25 to 5.0 mm, more preferably 0.5 to 3.0 mm and even more preferably 0.75 to 2.0 mm. If the heights are less than 0.25 mm, the protrusion of the ridges will be minimal, making it impossible to obtain a flexible feel on the skin by implementation of the shaped structure, while if the heights are greater than 5.0 mm, the ridges will protrude significantly, making it difficult to obtain a flexible feel on the skin.

The depths of the recesses 135, i.e. the distances from the furrow bottoms 133 of the furrows 131 to the bottom parts 137 of the recesses 135, is preferably 0.05 to 2.0 mm, more preferably 0.075 to 1.5 mm, and even more preferably 0.1 to 1.0 mm. If the distances are less than 0.05 mm, it will be difficult to ensure rigidity of the bottom parts 137, and the strength of the nonwoven fabric in the thickness direction will tend to be insufficient. If the distances are greater than 2.0 mm, on the other hand, the strength of the shaped nonwoven fabric in the thickness direction will tend to be insufficient.

Since the shaped nonwoven fabric 113 according to the third embodiment has a specific shaped structure, i.e. a structure comprising a plurality of ridges 129, a plurality of furrows 131 provided with furrow bottoms 133, and a plurality of recesses 135 arranged intermittently in each of the furrow bottoms 133, it is possible to buffer force in the thickness direction T of the shaped nonwoven fabric 113, that is applied from the second surface 117 side of the shaped nonwoven fabric 113, and even when force has been applied in the thickness direction T and the shaped structure has temporarily collapsed, the shaped structure is easily restored when the force is removed.

Moreover, since the shaped nonwoven fabric 113 according to the third embodiment has a specific shaped structure and can buffer force in the thickness direction T of the shaped nonwoven fabric 113 that is applied from the second surface 117 side of the shaped nonwoven fabric 113, sufficient flexibility can be ensured even when the shaped nonwoven fabric 113 is one that includes cellulosic fibers such as cotton.

The shaped nonwoven fabric according to the third embodiment can be produced by the method described in Japanese Patent Publication No. 5829326, Japanese Patent Publication No. 5829327 or Japanese Patent Publication No. 5829349.

In the nonwoven fabric of the present disclosure, the thermoplastic resin fibers are not particularly restricted so long as they are fibers made of a thermoplastic resin, and examples for the thermoplastic resin include olefin-based resins such as polyethylene (PE), polypropylene (PP) and ethylene-vinyl acetate copolymer (EVA); polyester-based resins such as polyethylene terephthalate (PET) and polylactic acid (PLA); and polyamide-based resins such as 6-nylon; as well as any desired combinations of these. The thermoplastic resin fibers may be hydrophilic or hydrophobic, and they may also be hydrophilicized with a hydrophilic agent.

The fineness of the thermoplastic resin fibers is not particularly restricted, but from the viewpoint of nonwoven fabric strength, flexibility, feel on the skin and liquid permeability, it will usually be in the range of 1.1 to 8.8 dtex and preferably 1.5 to 4.6 dtex.

The mean fiber length of the thermoplastic resin fibers is not particularly restricted, but from the viewpoint of nonwoven fabric strength, flexibility and liquid permeability, it is usually in the range of 20 to 100 mm and preferably 35 to 65 mm.

When the nonwoven fabric of the present disclosure has a multilayer structure, the fiber size of the thermoplastic resin fibers in the layers that include cellulosic fibers is preferably smaller than the fiber size of the thermoplastic resin fibers in the layers that do not include cellulosic fibers. The thermoplastic resin fibers with small fiber sizes in the layers that include cellulosic fibers readily tangle with the cellulosic fibers in the layers that include cellulosic fibers and the thermoplastic resin fibers in the layers that do not include cellulosic fibers, helping to prevent separation within the layers and separation between the layers that result from dissociation between the thermoplastic resin fibers and the cellulosic fibers, and allowing the nonwoven fabric to maintain excellent strength.

In the nonwoven fabric of the present disclosure, the cellulosic fibers are not particularly restricted so long as they are fibers that include cellulose, and for example, they may be natural cellulose fibers, regenerated cellulose fibers, refined cellulose fibers or semi-synthetic cellulose fibers.

Natural cellulose fibers may be plant fibers, such as seed hair fibers (for example, cotton) bast fiber (for example, hemp), leaf vein fibers (for example, Manila hemp) or fruit fibers (for example, coconut).

Cotton may be hirsutum cotton (for example, upland cotton), barbadense cotton, arboreum cotton or herbaceum cotton.

The cotton may also be organic cotton or Preorganic Cotton™.

Organic cotton means cotton that has been certified according to the GOTS (Global Organic Textile Standard).

The regenerated cellulose fibers may be fibers that are rayon such as viscose rayon obtained from viscose, polynosic and modal, or cuprammonium rayon obtained from cuprammonium salt solutions of cellulose, (also known as "cupra").

As refined cellulose fibers there may be mentioned lyocell, and specifically fiber formed by dissolving pulp in an aqueous solution of N-methylmorpholine N-oxide to produce a spinning stock solution (dope) and extruding into a dilute solution of N-methylmorpholine N-oxide. Such refined cellulose is commercially available as Tencel™, for example.

The semisynthetic fibers may be semi-synthetic cellulose, such as acetate fiber, examples of which include triacetate and diacetate fibers.

In the nonwoven fabric of the present disclosure, the cellulosic fibers preferably have a shorter mean fiber length than the thermoplastic resin fibers. This is because during production of the nonwoven fabric, opening of the cellulosic fibers will be inhibited and fiber masses of the cellulosic fibers will tend to form, resulting in fiber masses of the cellulosic fibers tending to be present in a dispersed state in the matrix of the thermoplastic resin fibers of the nonwoven fabric.

The cellulosic fibers preferably have a shorter mean fiber length than the thermoplastic resin fibers, and preferably have a mean fiber length of 10 to 50 mm and more preferably 20 to 28 mm. When the cellulosic fibers are cotton, cotton with a mean fiber length of 20.6 to 25.4 mm is referred to as "medium fiber cotton", while cotton with a mean fiber length of 26.2 to 27.8 mm is referred to as "medium-long fiber cotton".

The cellulosic fibers are preferably natural cellulose fibers, more preferably cotton, even more preferably cotton and yet more preferably hirsutum seed cotton. This is from the viewpoint of the feeling of assurance, fluid absorption property and retentivity of natural materials.

According to the present disclosure, the mean fiber length of fibers is measured according to "A7.1.1, Method A (Standard method) Method for measuring lengths of individual fibers on graduated glass plate", under "A7.1 Fiber length measurement" in appendix A of JIS L 1015:2010.

This method is the test method corresponding to ISO 6989 published in 1981.

The nonwoven fabric of the present disclosure includes the cellulosic fibers at preferably 3 to 35 mass %, more preferably 3 to 20 mass % and even more preferably 3 to 10 mass %. This is from the viewpoint that moisture that has a tendency to be released from the absorbent body, to pass through the liquid-impermeable sheet having moisture vapor permeability and to be discharged to the outside of the absorbent article, is easily absorbed and held by the fiber masses of cellulosic fibers, in a concentrated (spot-like) manner through the gaps, and the area of the portions holding the moisture in the planar direction of the nonwoven fabric can be reduced (to spot-like forms). Thus, even while moisture that has been released from the absorbent body is caused to pass through the liquid-impermeable sheet having moisture vapor permeability and is discharged, it is possible to reduce the amount of moisture that passes through the nonwoven fabric and is discharged to the outside of the absorbent article.

When the nonwoven fabric of the present disclosure comprises thermoplastic resin fibers and cellulosic fibers, the thermoplastic resin fibers and cellulosic fibers are included in ratio s of preferably 65 to 97 mass % and 3 to 35 mass %, more preferably 80 to 97 mass % and 3 to 20 mass % and even more preferably 90 to 97 mass % and 3 to 10 mass %, respectively.

The nonwoven fabric of the present disclosure may include third fibers, in addition to the thermoplastic resin fibers and cellulosic fibers.

The nonwoven fabric of the present disclosure preferably has junctions where the thermoplastic resin fibers are joined together, at the portions other than the fiber masses of the cellulosic fibers. The junctions may be junctions by an adhesive, or fusion points between the thermoplastic resin fibers.

In the nonwoven fabric of the present disclosure, the cellulosic fibers may be included in portions other than the fiber masses of the cellulosic fibers, such as in the matrix of the thermoplastic resin fibers.

The nonwoven fabric of the present disclosure is a nonwoven fabric for an outer sheet of an absorbent article comprising a liquid-impermeable sheet having moisture vapor permeability, the liquid-impermeable sheet having a moisture permeability of preferably 1,500 to 4,500 $g/m^2/24$ h, more preferably 2,000 to 4,000 $g/m^2/24$ h and even more preferably 2,500 to 3,800 $g/m^2/24$ h. These ranges are from the viewpoint of the effect of the present disclosure.

The moisture permeability used is the value measured in a manner based on JIS Z 0208:1976, "Test method for moisture permeability of moisture-proof packaging materials (cup method)", but it differs from JIS Z 0208:1976 in the following aspects.

(i) A moisture permeation cup is filled with 20 g of water instead of calcium chloride.

(ii) The moisture permeability is measured in a steady temperature and humidity room at a temperature of 40° C. and a relative humidity of 60%.

(iii) After standing for 24 hours, the weight reduction of the 20 g of water (discharge), instead of the weight increase of the cup, is measured.

The liquid-impermeable sheet may be a film such as a polyolefin-based film, or a nonwoven fabric such as a spunbond or spunlace nonwoven fabric. When the liquid-impermeable sheet is a film, it preferably has moisture permeability, such as a moisture-permeable film.

The liquid-impermeable sheet is preferably one without any liquid permeability.

The nonwoven fabric of the present disclosure has a basis weight in the range of generally 10 to 100 $g/m^2$, preferably 15 to 75 $g/m^2$ and more preferably 20 to 50 $g/m^2$. These ranges are from the viewpoint of the effect of the present disclosure.

The nonwoven fabric of the present disclosure has a thickness of generally 0.1 to 5.0 mm, preferably 0.5 to 3.0 mm and more preferably 0.8 to 2.0 mm, although this is not restrictive. These ranges are from the viewpoint of the effect of the present disclosure. When the nonwoven fabric of the present disclosure is a shaped nonwoven fabric, its thickness is the thickness of the nonwoven fabric before shaping.

As used herein, the thickness (mm) of the nonwoven fabric is that measured in the following manner.

An FS-60DS by Daiei Kagaku Seiki Mfg. Co., Ltd. is prepared [measuring surface: 44 mm (diameter), measuring pressure: 3 $g/cm^2$], five different locations of the absorbent body are pressed under standard conditions (temperature: 23±2° C., relative humidity: 50±5%), the thickness is measured after 10 seconds of pressing at each site, and the mean value of the five measured values is recorded as the thickness of the absorbent body.

In the nonwoven fabric of the present disclosure, the fiber masses of the cellulosic fibers are preferably dispersed in the nonwoven fabric, and the nonwoven fabric of the present disclosure more preferably includes a matrix composing the nonwoven fabric and fiber masses of cellulosic fibers that are dispersed in the matrix. This is so that moisture that has a tendency to be released from the absorbent body and to pass through the liquid-impermeable sheet having moisture vapor permeability and to be discharged will be absorbed and held in a concentrated (spot-like) manner at the fiber masses of the cellulosic fibers, and will be able to reduce the area of the portions that absorb and hold moisture (to spot-like forms) in the in-plane direction of the nonwoven fabric, while moisture that has been released from the absorbent body will be caused to pass through the liquid-impermeable sheet having moisture vapor permeability and to be discharged, while reducing the amount of moisture that passes through the nonwoven fabric and is discharged to the outside of the absorbent article.

The matrix can be composed of fibers in the nonwoven fabric of the present disclosure, and for example, it may be composed of thermoplastic resin fibers and cellulosic fibers, although it is preferably composed of thermoplastic resin fibers. This is from the viewpoint of the effect of the present disclosure.

A nonwoven fabric of the present disclosure comprising a two-layer structure with a clothing side layer having a clothing-contacting surface and a skin side layer disposed further on the skin side than the clothing side layer, can be produced by the following production method.

The production method described below is merely an example of a method of producing the nonwoven fabric of the present disclosure, and the nonwoven fabric of the present disclosure may be produced by any desired method.

(1) A nonwoven fabric production apparatus is prepared that comprises a conveyor belt capable of transporting a sheet member with tension adjustment, and comprising, in order, a first stage carding apparatus, a second stage carding apparatus, an air-through system heating apparatus, a compression apparatus comprising a pair of anvil rolls, and a bulk recovery apparatus (thickness recovery apparatus) with heating means, along the conveyor belt.

(2) Core-sheath thermoplastic resin fibers and cellulosic fibers are supplied to the first stage carding apparatus, and the thermoplastic resin fibers and cellulosic fibers are opened to form on the conveyor belt a first web that can form a skin side layer. Incidentally, if the mean fiber length of the cellulosic fibers is shorter than the mean fiber length of the thermoplastic resin fibers, it will be possible to minimize opening of the cellulosic fibers and to help the fiber masses of the cellulosic fibers remain in the first web.

(3) Core-sheath thermoplastic resin fibers and cellulosic fibers are supplied to the second stage carding apparatus, and the thermoplastic resin fibers and cellulosic fibers are opened to stack a second web that can form a clothing side layer, on the first web on the conveyor belt, and thereby form a stacked web.

(4) The stacked web is conveyed to the air-through system heating apparatus, the stacked web is heated to a temperature higher than the melting point of the sheath portion of the core-sheath thermoplastic resin fibers, causing heat fusion between the thermoplastic resin fibers in the first web and second web, and forming the nonwoven fabric to be processed.

(5) The nonwoven fabric to be processed is compressed in its thickness direction using the pair of anvil rolls of the compression apparatus, compressing the thickness of the nonwoven fabric to be processed by about 10 to 40%, for example (=100×compressed nonwoven fabric thickness/thickness of nonwoven fabric to be processed), and the matrix composed mainly of thermoplastic resin fibers and the fiber masses of cellulosic fibers is compressed to form a compressed nonwoven fabric.

The compressed nonwoven fabric may be wound onto a roll and the compressed nonwoven fabric subjected to further compression. When wound onto a roll, the thickness of the compressed nonwoven fabric is preferably further compressed to 30 to 50%.

(6) The compressed nonwoven fabric is subjected to strong tension in the machine direction to cut the fused sections formed between the thermoplastic resin fibers and the fiber masses of the cellulosic fibers, and form a nonwoven fabric cut at the fused sections between the cellulosic fibers and fiber masses.

(7) The nonwoven fabric cut at the fused sections between the cellulosic fibers and fiber masses is conveyed to the bulk recovery apparatus, the nonwoven fabric is heated, and the thickness of the nonwoven fabric recovers to 130 to 200%, for example (=100×thickness of nonwoven fabric of the present disclosure/nonwoven fabric cut at the fused sections between the cellulosic fibers and fiber masses), to form gaps between the thermoplastic resin fibers that have easy thickness recoverability and the fiber masses that have poor thickness recoverability, thereby forming a nonwoven fabric of the present disclosure.

When the nonwoven fabric of the present disclosure comprises a three-layer structure with a clothing side layer having a clothing-contacting surface, a skin side layer disposed on the skin side and an intermediate layer between them, a third stage carding apparatus may be situated between the second stage carding apparatus and the air-through system heating apparatus.

The method of forming the web of each layer is not limited to the method described above, and a wet method, for example, may be used. The method of forming the nonwoven fabric is also not restricted to the method described above, and a hydroentangling method or needle punching method, for example, may be employed.

Also, after step (7), a nonwoven fabric shaping step may be provided according to the method described in Japanese Patent Publication No. 5829326, Japanese Patent Publication No. 5829327 or Japanese Patent Publication No. 5829349.

The nonwoven fabric of the present disclosure is suitable for the outer sheet of an absorbent article, in which case the absorbent article is not particularly restricted and may be a disposable diaper, urine-absorbing pad, sanitary napkin or panty liner, for example.

EXAMPLES

The present disclosure will now be explained in fuller detail by examples, with the understanding that the disclosure is not meant to be limited to the examples.

Production Example 1

<Production of Nonwoven Fabric>

Two different PET/PE core-sheath composite fibers of different fineness (composite fiber A with fineness: 2.2 dtex, mean fiber length: 45 mm, composite fiber B with fineness: 1.7 dtex, mean fiber length: 45 mm), and hirsutum seed cotton (mean fiber length=~27 mm) were supplied to a first stage carding apparatus, and the fibers were opened to form a first web (skin side layer, basis weight: 13 g/m$^2$, basis weight of composite fiber A and composite fiber B: 10 g/m$^2$, hirsutum seed cotton basis weight: 3 g/m$^2$).

PET/PE core-sheath composite fibers (fineness: 2.8 dtex, mean fiber length: 45 mm) were supplied to a second stage carding apparatus as thermoplastic resin fibers, and the PET/PE core-sheath composite fibers were opened to form a second web (clothing side layer, basis weight: 20 g/m$^2$) on the first web, forming a stacked web.

The stacked web was conveyed to an air-through system heating apparatus, and PET/PE core-sheath composite fibers within each web and between the webs were heat-fused in the heating apparatus to obtain a nonwoven fabric to be processed No. 1.

The nonwoven fabric to be processed No. 1 was compressed in its thickness direction with a pair of anvil rolls, compressing the thickness to approximately 20%. Next, the nonwoven fabric to be processed No. 1 was subjected to tension in the planar direction and heated to restore its thickness, forming nonwoven fabric No. 1.

Figure 11:
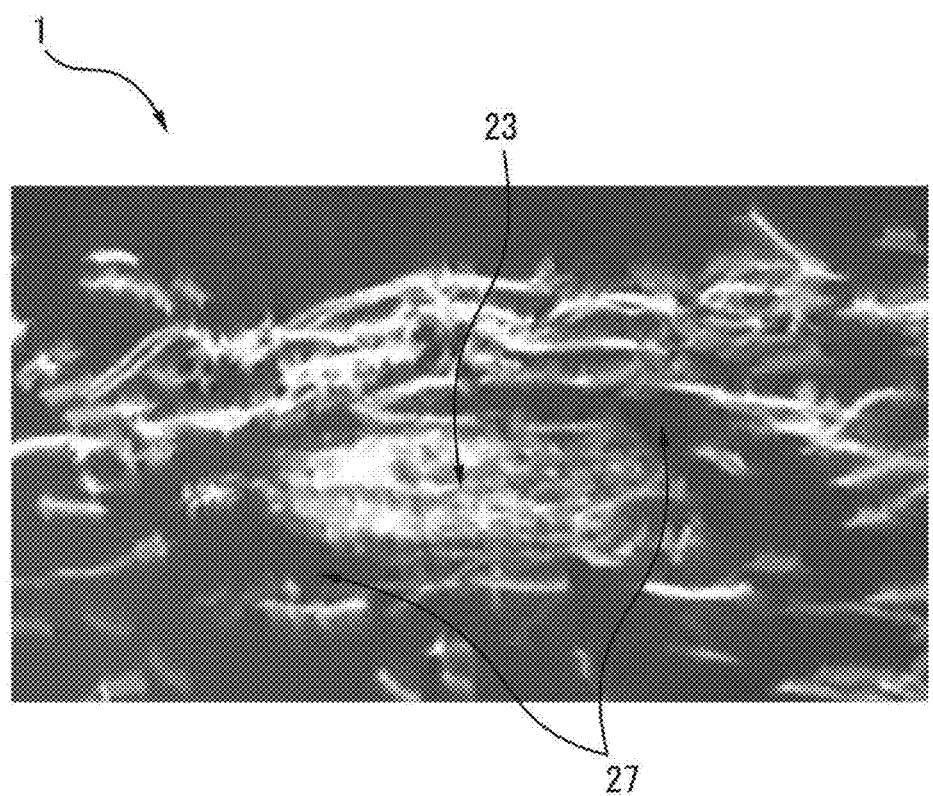
FIG. 11 is an image of nonwoven fabric No. 1 produced in Production Example 1, photographed with a 3D measurement X-ray CT device.

Nonwoven fabric No. 1 was scanned with a 3D measurement X-ray CT device (TDM-1000-IS/SP by Yamato Scientific Co., Ltd.) to obtain a three-dimensional image near fiber masses. The image is shown in FIG. 11. From FIG. 11 it is seen that gaps 27 are present adjacent to the fiber masses 23.

<Production of Disposable Diaper>

An absorbent material comprising pulp with a basis weight of 220 g/m$^2$ and a superabsorbent polymer (SAP) with a basis weight of 156 g/m$^2$ was covered with tissue having a basis weight of 10 g/m$^2$, to obtain an absorbent body. Nonwoven fabric No. 1 was joined to one side of the obtained absorbent body as a liquid-permeable sheet, with the first surface (the clothing side layer formed from the first web) contacting the absorbent body, a moisture-permeable film with a basis weight of 15 g/m² (moisture permeability: ~3,000 g/m²/24 h) was joined to the other side of the absorbent body as a liquid-impermeable sheet, and nonwoven fabric No. 1 was joined to the outside of the moisture-permeable film as an outer film, to obtain a laminate. The joining was formed using a hot-melt adhesive (coating amount: 3 g/m²).

The obtained laminate was cut to the prescribed shape of a disposable diaper, to fabricate disposable diaper No. 1.

Production Example 2

Nonwoven fabric No. 1 produced in Production Example 1 was subjected to shaping treatment by the method described in Japanese Patent Publication No. 5829326, to produce nonwoven fabric No. 2.

Disposable diaper No. 2 was then produced in the same manner as Production Example 1, except that the liquid-permeable sheet and outer film were changed from nonwoven fabric No. 1 to nonwoven fabric No. 2. Incidentally, nonwoven fabric No. 2 was joined as a liquid-permeable sheet, with the first surface (the clothing side layer formed from the first web) contacting with the absorbent body, and as an outer film, with the first surface (the clothing side layer formed from the first web) contacting with the liquid-impermeable sheet.

Comparative Production Example 1

Nonwoven fabric No. 3 was formed in the same manner as Production Example 1, except that the first web (basis weight: 10 g/m²) was formed from a mixture of two different PET/PE core-sheath composite fibers of different fineness (composite fiber A with fineness: 2.2 dtex, mean fiber length: 45 mm and composite fiber B with fineness: 1.7 dtex, mean fiber length: 45 mm). Disposable diaper No. 3 was produced in the same manner as Production Example 1, except that the liquid-permeable sheet and outer film were changed from nonwoven fabric No. 1 to nonwoven fabric No. 3.

Examples 1 and 2, and Comparative Example 1

Artificial urine was absorbed with disposable diapers No. 1 to No. 3, and the transpiration rate (mass %) was evaluated at different time points. The results are shown in Table 1.

[Transpiration Rate Measurement Method]

(1) In order to eliminate the effect of the surrounding environment, the sample is set in a thermo-hygrostat at a temperature of 20° C. and a humidity of 60% RH for 5 days (120 hours).

(2) The sample is removed from the thermo-hygrostat, and the initial mass $A_0$ (g) of the sample is measured.

(3) The sample is spread out on a test stage having a horizontal plane, with the liquid-permeable sheet on the upper side, and a cylinder with an inner diameter of 60 mm is placed on the liquid-permeable sheet.

(4) Into the cylinder there is dropped 80 mL of artificial urine for 10 seconds.

The artificial urine is prepared by dissolving 200 g of urea, 80 g of sodium chloride, 8 g of magnesium sulfate, 3 g of calcium chloride and approximately 1 g of dye (Blue #1) in 10 L of ion-exchanged water.

(5) Upon confirming that all of the artificial urine in the cylinder has been absorbed by the sample, the cylinder is removed from the top of the liquid-permeable sheet and the sample mass $A_1$ (g) of the absorbent article after absorption of the artificial urine is immediately measured.

(6) The sample after artificial urine absorption is allowed to stand in a constant atmosphere, and the sample masses $W_1$, $W_3$, $W_5$, $W_8$ and $W_{21}$ (g) after 1 hour, after 3 hours, after 5 hours, after 8 hours and after 21 hours, respectively, are measured from the point where the cylinder was removed from the top of the front sheet in (5) above.

(7) The transpiration rates $E_1$, $E_3$, $E_5$, $E_8$ and $E_{21}$ (mass %) at each elapsed time point for the sample is calculated by the following formula (1).

$$E_N(\text{mass \%}) = 100 \times (A_1 - W_N)/(A_1 - A_0)$$

(Here, N is 1, 3, 5, 8 or 21.)

TABLE 1

| Example No. | | Example 1 | Example 2 | Comp. Example 1 |
|---|---|---|---|---|
| Disposable diaper No. | | No. 1 | No. 2 | No. 3 |
| Liquid-permeable sheet | Nonwoven fabric No. | No. 1 | No. 2 | No. 3 |
| | Skin side layer | PET/PE composite fiber | PET/PE composite fiber | PET/PE composite fiber |
| | Basis weight (g/m²) | 20 | 20 | 20 |
| | Clothing side layer | Two-component PET/PE composite fiber + cotton | Two-component PET/PE composite fiber + cotton | Two-component PET/PE composite fiber |
| | Basis weight (g/m²) | 10 + 3 | 10 + 3 | 10 |
| | Total basis weight (g/m²) | 33 | 33 | 30 |
| | Shaping | No | Yes | No |
| Outer sheet | Nonwoven fabric No. | No. 1 | No. 2 | No. 3 |
| | Clothing side layer | PET/PE composite fiber | PET/PE composite fiber | PET/PE composite fiber |
| | Basis weight (g/m²) | 20 | 20 | 20 |
| | Skin side layer | Two-component PET/PE composite fiber + cotton | Two-component PET/PE composite fiber + cotton | Two component PET/PE composite fiber |
| | Basis weight (g/m²) | 10 + 3 | 10 + 3 | 10 |
| | Total basis weight (g/m²) | 33 | 33 | 30 |
| | Shaping | No | Yes | No |
| Transpiration rate (%) | After 1 hr | 1.5 | 1.1 | 2.3 |
| | After 3 hrs | 3.2 | 2.8 | 4.5 |
| | After 5 hrs | 6.3 | 5.8 | 7.6 |
| | After 8 hrs | 9.5 | 8.2 | 11.6 |
| | After 21 hrs | 27.4 | 25.4 | 35.4 |

As shown in Table 1, disposable diapers No. 1 and No. 2 had low transpiration rates after artificial urine absorption compared to disposable diaper No. 3, and were more resistant to dampness and mustiness. In particular, disposable diapers No. 1 and No. 2 had low transpiration rates after 8 hours and after 21 hours from absorption of artificial urine, and tended not to exhibit any condition of dampness or mustiness over a prolonged period.

When the liquid-permeable sheet was changed to a common air-through nonwoven fabric in the technical field for disposable diapers No. 1 to No. 3, the same transpiration rates tended to be obtained as the results obtained in Example 1, Example 2 and Comparative Example 1.

REFERENCE SIGNS LIST

1 Absorbent article
3 Liquid-permeable sheet
5 Liquid-impermeable sheet
6 Outer sheet
7 Absorbent body
9 Skin side surface
11 Clothing-contacting surface
13 Nonwoven fabric
15 First surface
17 Second surface
19 Thermoplastic resin fibers
21 Cellulosic fibers
23 Fiber masses
25 First region
26 Second region
27 Gap
101 Absorbent article
103 Liquid-permeable sheet
105 Liquid-impermeable sheet
106 Outer sheet
107 Absorbent body
113 Shaped nonwoven fabric
113a Clothing side layer
113b Intermediate layer
113c Skin side layer
115 First surface
117 Second surface
129 Ridge
130 Depression
131 Furrow
133 Furrow bottom
135 Recess
137 Bottom part
139 Perimeter wall section
141 First perimeter wall section
142 Second perimeter wall section
143 Hole
145 Separated region
201 Anti-leakage wall
203 Elastic member
205 Anchoring part
207 Elastic member
209 Tape fastener
T Thickness direction
P Planar direction
$EE_1$, $EE_2$ Outer edge
$D_O$ One direction
$D_A$ Other direction

The invention claimed is:

1. A nonwoven fabric for an outer sheet of an absorbent article comprising a liquid-impermeable sheet having moisture vapor permeability, wherein
the nonwoven fabric has a thickness direction and a planar direction, and a first surface and a second surface,
the nonwoven fabric includes thermoplastic resin fibers, and cellulosic fibers of which at least a portion form a plurality of separate fiber masses,
the nonwoven fabric comprises a plurality of gaps that are adjacent to first regions of each of the plurality of separate fiber masses that are facing the first surface,
each of the plurality of separate fiber masses are not joined with the thermoplastic resin fibers,
the nonwoven fabric comprises a matrix including at least the thermoplastic resin fibers, and
the plurality of separate fiber masses are dispersed in the matrix of the thermoplastic resin fibers.

2. The nonwoven fabric according to claim 1, wherein outer edges of the gaps in the planar direction are situated further outward than outer edges of the plurality of separate fiber masses in the planar direction.

3. The nonwoven fabric according to claim 1, wherein the nonwoven fabric further comprises further gaps adjacent to second regions of at least some of the plurality of separate fiber masses that are facing the second surface.

4. The nonwoven fabric according to claim 1, wherein the thermoplastic resin fibers are joined together.

5. The nonwoven fabric according to claim 1, wherein the nonwoven fabric includes the cellulosic fibers in a ratio of 3 to 35 mass %.

6. The nonwoven fabric according to claim 1, wherein the cellulosic fibers have a shorter mean fiber length than the thermoplastic resin fibers.

7. The nonwoven fabric according to claim 1, wherein the cellulosic fibers include organic cotton.

8. The nonwoven fabric according to claim 1, wherein the cellulosic fibers include hirsutum cotton.

9. The nonwoven fabric according to claim 1, wherein
the nonwoven fabric has a multilayer structure including a clothing side layer with a clothing-contacting surface, and
the nonwoven fabric comprises the plurality of separate fiber masses in a layer other than the clothing side layer.

10. The nonwoven fabric according to claim 1, wherein the nonwoven fabric comprises
a plurality of protrusions protruding in a direction from the first surface toward the second surface, and
a plurality of depressions that are depressed in a direction from the second surface toward the first surface, each of the plurality of protrusions and each of the plurality of depressions overlapping in the thickness direction.

11. The nonwoven fabric according to claim 10, wherein
each of the plurality of protrusions forms a ridge running in one direction,
the nonwoven fabric comprises a plurality of furrows having furrow bottoms between adjacent ridges, and
each of the plurality of furrows comprises a plurality of recesses, depressed in a direction from the first surface toward the second surface, the plurality of recesses being arranged intermittently in one direction on the furrow bottoms, each of the plurality of recesses having a bottom part.

12. An absorbent article, comprising a liquid-permeable sheet, an absorbent body, a liquid-impermeable sheet, and an outer sheet, in that order, wherein
the outer sheet is the nonwoven fabric according to claim 1.

13. The absorbent article according to claim 12, wherein the second surface of the nonwoven fabric constitutes an outer surface of the outer sheet.

14. An absorbent article, comprising a liquid-permeable sheet, an absorbent body, a liquid-impermeable sheet, and an outer sheet, in that order, wherein each of the outer sheet and the liquid-permeable sheet is the nonwoven fabric according to claim 1.

15. The nonwoven fabric according to claim 1, wherein the gaps are located between the thermoplastic resin fibers and each of the first regions of the plurality of separate fiber masses.

* * * * *